(12) United States Patent
Fujisawa et al.

(10) Patent No.: US 9,339,249 B2
(45) Date of Patent: *May 17, 2016

(54) MEDICAL IMAGE PROCESSING APPARATUS

(71) Applicants: Kabushiki Kaisha Toshiba, Tokyo (JP); Toshiba Medical Systems Corporation, Otawara-shi (JP)

(72) Inventors: Yasuko Fujisawa, Nasushiobara (JP); Tatsuya Kimoto, Otawara (JP); Shinsuke Tsukagoshi, Nasushiobara (JP); Yoshihiro Ikeda, Sakura (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 373 days.

This patent is subject to a terminal disclaimer.

(21) Appl. No.: 13/774,137

(22) Filed: Feb. 22, 2013

(65) Prior Publication Data

US 2013/0223586 A1 Aug. 29, 2013

(30) Foreign Application Priority Data

Feb. 24, 2012 (JP) .................................. 2012-038632
Feb. 24, 2012 (JP) .................................. 2012-038692

(51) Int. Cl.
*A61B 6/00* (2006.01)
*A61B 6/03* (2006.01)
*G06K 9/00* (2006.01)

(52) U.S. Cl.
CPC . *A61B 6/52* (2013.01); *A61B 6/032* (2013.01); *A61B 6/488* (2013.01); *A61B 6/505* (2013.01); *A61B 6/5205* (2013.01); *A61B 6/545* (2013.01)

(58) Field of Classification Search
CPC .......... A61B 6/032; A61B 6/488; A61B 6/03; A61B 6/463; A61B 6/52; A61B 6/545; A61B 6/505; A61B 6/5205; G06K 2209/05; G06K 9/3216; G06T 11/003
See application file for complete search history.

(56) References Cited

U.S. PATENT DOCUMENTS 5,602,935 A * 2/1997 Yoshida ................. A61B 6/505
382/132
5,724,930 A 3/1998 Sakurai et al.
(Continued)

FOREIGN PATENT DOCUMENTS

JP 2005-342088 A 12/2005
JP 2006-102353 A 4/2006
(Continued)

OTHER PUBLICATIONS

Office Action mailed Dec. 15, 2015 in Japanese Patent Application No. 2012-038692.

*Primary Examiner* — Amara Abdi
(74) *Attorney, Agent, or Firm* — Oblon, McClelland, Maier & Neustadt, L.L.P.

(57) ABSTRACT

The medical image processing apparatus according to the embodiment comprises a photographing unit that scans the flexible sites of the living body including the plurality of components and obtains the projected data, a reconstruction processing unit that carries out reconstruction processing on the projected data and generated first image data of the plurality of timing points of the flexible sites, and an analyzing unit that compares the first image data of the plurality of timing points and the second image data showing the flexible sites, thereby specifying the data with the timing point shown in the second image data from among the first image data of the plurality of timing points.

20 Claims, 17 Drawing Sheets

(56) References Cited

U.S. PATENT DOCUMENTS

| | | | | |
|---|---|---|---|---|
| 2005/0263730 A1* | 12/2005 | Sendai | ............ | G03B 42/08 250/583 |
| 2010/0202675 A1* | 8/2010 | Takanaka | ............ | A61B 6/032 382/130 |
| 2010/0232566 A1* | 9/2010 | Hirokawa | ............ | A61B 6/032 378/5 |
| 2012/0008741 A1* | 1/2012 | Hendriks | ............ | A61B 6/4441 378/63 |
| 2013/0223589 A1 | 8/2013 | Fujisawa et al. | | |

FOREIGN PATENT DOCUMENTS

| | | |
|---|---|---|
| JP | 2010-154992 A | 7/2010 |
| JP | 2010-201157 | 9/2010 |
| JP | 2010-284301 | 12/2010 |
| JP | 2013-172818 A | 9/2013 |
| WO | 2010/067281 A1 | 6/2010 |

* cited by examiner

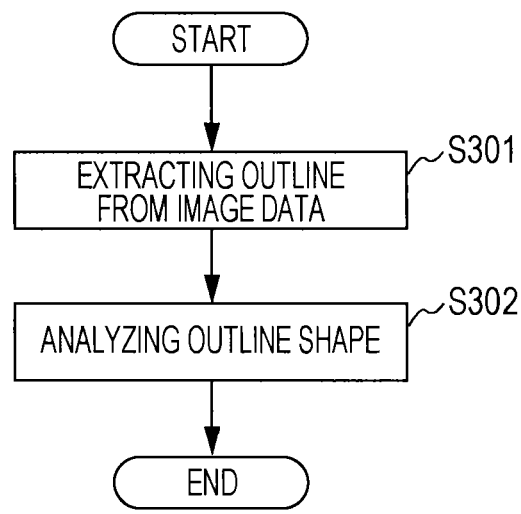
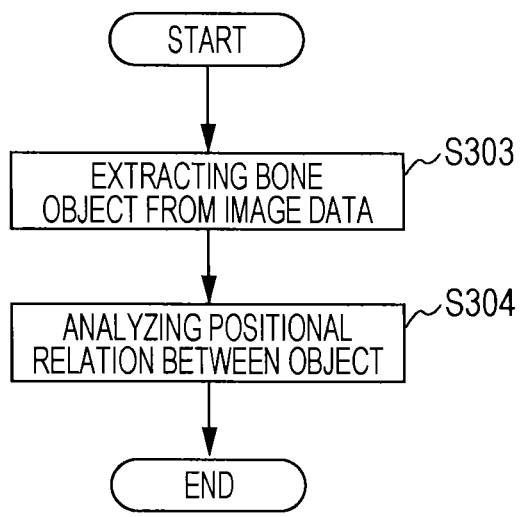

MEDICAL IMAGE PROCESSING APPARATUS

CROSS-REFERENCE TO RELATED APPLICATION

This application is based upon and claims the benefit of priority from Japanese Patent Applications No. 2012-038632 and No. 2012-038692, filed on Feb. 24, 2012; the entire contents of which are incorporated herein by reference.

FIELD

The present embodiment relates to the technology of a medical image processing apparatus for generating medical images.

BACKGROUND

An apparatus that uses an X-ray CT (Computed Tomography) system to scan test objects and processes the accumulated data with a computer, thereby imaging the inside of the test object.

Specifically, the X-ray CT system exposes X-rays onto the test object from different angles multiple times, extracts the X-rays penetrating the test object to an X-ray detector, and accumulates multiple detection data. The accumulated detection data is A/D-converted in a data accumulating unit, then sent to a console apparatus. The console apparatus carries out pretreatment, etc. on the detected data and produces projected data. Then, the console apparatus carries out reconstruction processing based on the projected data and produces volume data based on tomographic image data or a plurality of tomographic image data. The volume data is data set expressing a 3-dimensional distribution of a CT number corresponding to a 3-dimensional region of the test object.

Moreover, the X-ray CT system includes an apparatus such as a multi-slice X-ray CT system that can carry out high-definition (high resolution) imaging over a wide range per unit time. This multi-slice X-ray CT system uses detector elements in m column in an anteroposterior direction and the n rows in the direction orthogonally intersecting the anteroposterior direction as the detector used in the single slice X-ray CT system, that is, a two-dimensional detector of a configuration with the m columns and n rows arranged.

Due to such a multi-slice X-ray CT system, the larger a detector is (the greater the number of detector elements configuring the detector), the greater the possibility of acquiring projection data over a wider region in a single image. In other words, by temporarily imaging using a multi-slice X-ray CT system provided with such a detector, it is possible to generate volume data for a specific site at a high frame rate (hereinafter, sometimes referred to as a "Dynamic Volume scan"). This makes it possible to assess the movement of the specific region within a unit of time by means of 3-dimensional images.

Moreover, a medical image processing apparatus exists that reconstructs volume data based on the projected data obtained from the X-ray CT system and generated medical images from the volume data.

Meanwhile, when flexible sites configured by a plurality of parts such as joints, etc. are subjected to observation and the movements thereof are evaluated, there is a demand for displaying small movements, allowing for observation, by increasing the frame rate when each part of the observation subject attains the positional relation determined by an operator. Specifically, for example, when there is a reaction from a patient when the joints of the arm are bent by the patient (for example, a reaction of the patient such as "it hurts"), there is a desire to allow a close investigation into the condition of the bone before and after the reaction.

Moreover, the speed of movements of the observation subject such as the joints, etc. are not always constant, and when a series of movements are displayed at the same frame rate, the detailed movement of the observation subject may be difficult to observe regarding the timing points at which the observation subject rapidly moves. Accordingly, there is a desire to allow observation of detailed movements by increasing the frame rate as the observation subject rapidly moves. Moreover, at this time, for example, there is a desire for displaying the observation subject at a higher resolution in order to allow observation of more detailed movements. Furthermore, the frame rate and resolution are determined by reconstruction conditions. Moreover, when the frame rate or the resolution is increased, the processing load related to reconstruction increases, thereby prolonging the processing time. Accordingly, the reconstruction conditions are determined in advance in correspondence with the time required to generate the medical images and required image quality.

In this manner, there are cases when there is a desire for displaying, allowing for observation of detailed movements of the observation subject, by changing the reconstruction conditions in correspondence with the positional relation based on absolute positions such as "the positional relation determined in advance", etc. and relative positional relation of the observation subject between each timing point such as "speed of movement of the observation subject", etc. Furthermore, the frame rate of the displayed image is determined based on the frame rate of the acquired volume data (that is, the volume rate). Furthermore, hereinafter, the volume data may be referred to as "image data".

BRIEF DESCRIPTION OF THE DRAWINGS

FIG. 4B is a flow chart showing the operations related to the analysis of the positional relation regarding Embodiment 1.

FIG. 4C is a flow chart showing the operations related to the analysis of the positional relation regarding Embodiment 2.

DETAILED DESCRIPTION

The purpose of the present embodiment is to allow generation of the image data by changing the reconstruction conditions in correspondence with the positional relation of the observation subject based on the projected data chronologically obtained by the X-ray CT system. Moreover, another purpose is to provide the X-ray CT system allowing controlling of the operation related to acquiring the projected data in correspondence with the positional relation of the observation subject during acquiring of the projected data.

The medical image processing apparatus according to the embodiment comprises a photographing unit that scans the flexible sites of the living body including the plurality of components and obtains the projected data, a reconstruction processing unit that carries out reconstruction processing on the projected data and generated first image data of the plurality of timing points of the flexible sites, and an analyzing unit that compares the first image data of the plurality of timing points and the second image data showing the flexible sites, thereby specifying the data with the timing points shown in the second image data from among the first image data of the plurality of timing points.

(Embodiment 1)

Figure 1A:
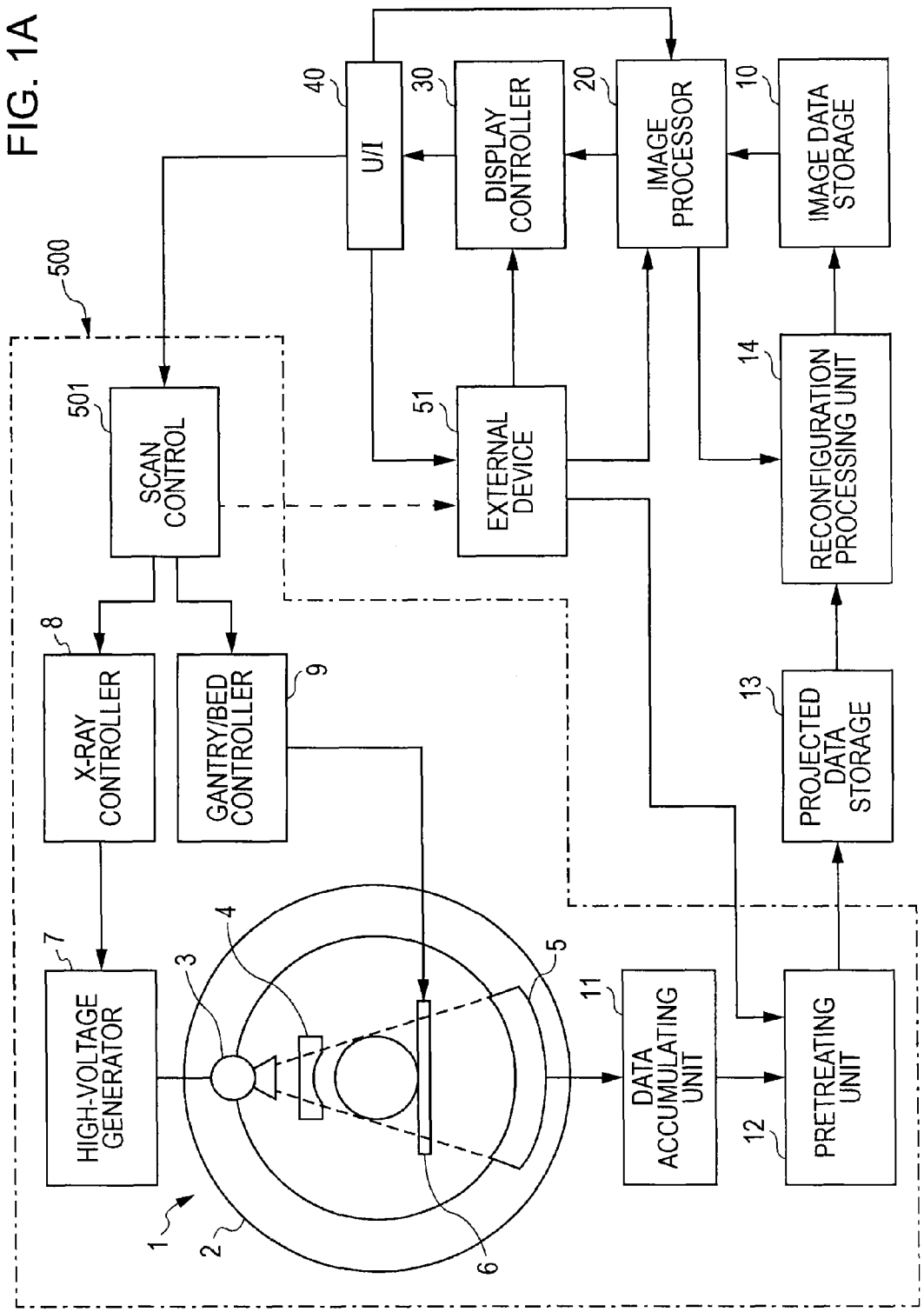
FIG. 1A is a block diagram of the X-ray CT system according to the present embodiment.
Figure 1B:
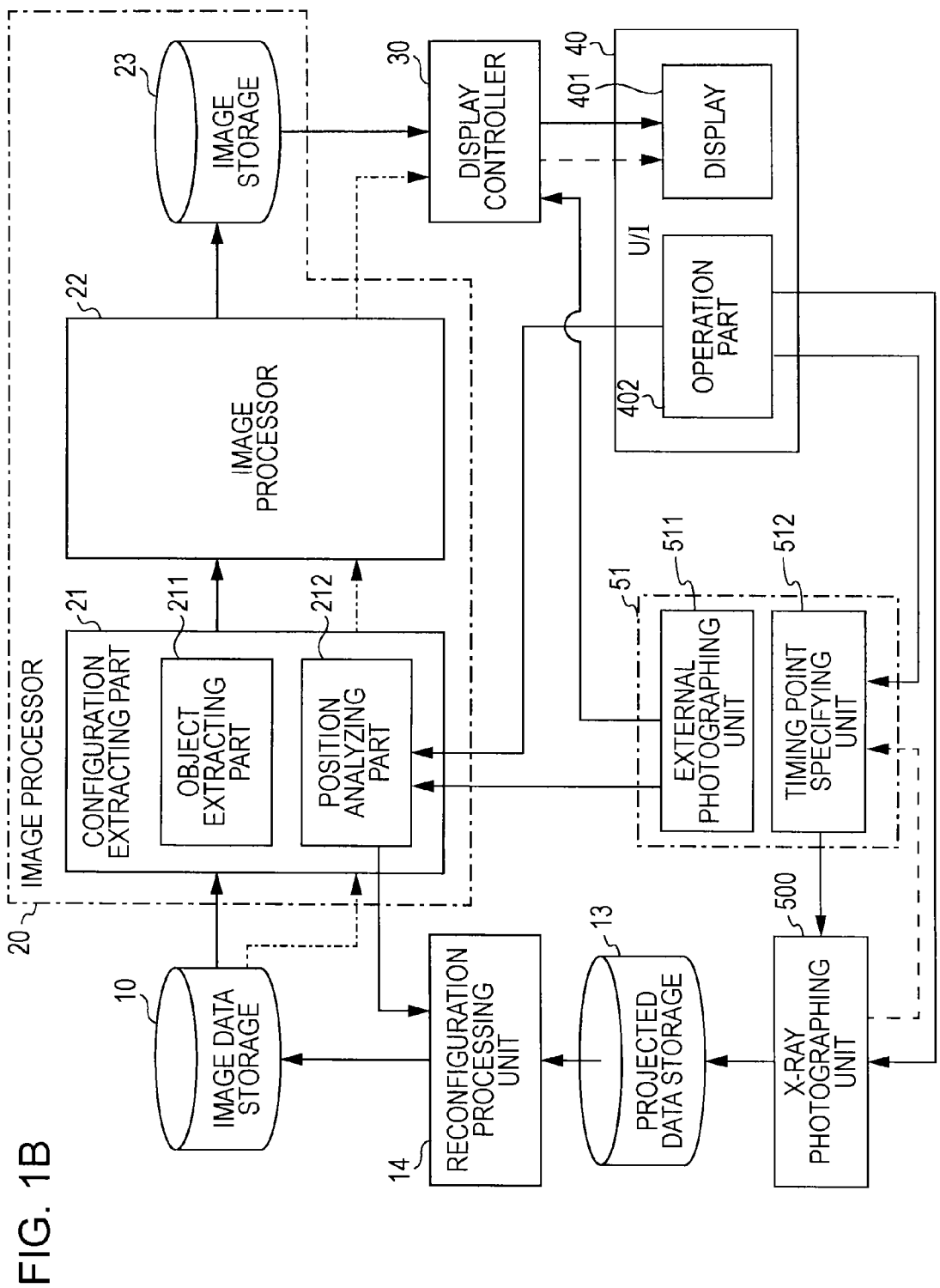
FIG. 1B is a block diagram showing the detailed configuration of the image processor.

The medical image processing apparatus according to Embodiment 1 reconstructs the projected data obtained from the X-ray CT system to generate the volume data, and generates medical images based on the volume data. Hereinafter, the configuration of the medical image processing apparatus according to the present embodiment will be explained with reference to FIG. 1A and FIG. 1B together with the configuration of the X-ray CT system. As illustrated in FIG. 1A, the medical image processing apparatus according to the present embodiment operates together with the X-ray photographing unit 500 (that is, the X-ray CT system) and an external apparatus 51, and comprises a projected data storage 13, a reconstruction processing unit 14, an image data storage 10, an image processing unit 20, a display control 30, and a U/I 40. In addition, the U/I 40 is a user interface including a display 401 and an operation part 402.

An X-ray CT scan is used as an example for describing the present embodiment, but an MRI scan may be used for the present embodiment instead of an X-ray CT scan. An MRI scan uses the nuclear magnetic resonance (NMR) phenomenon to magnetically activate a nuclear spin in the desired inspection part of the test object placed in the magnetostatic field using a high frequency signal of Larmor frequency, calculates the density distribution, the distribution of relaxation time, etc. based on FID (free induction decay) signals and echo signals generated along with the activation, and displays the image of any section of the test object from the measured data.

(X-Ray Photographing Unit 500)

An explanation is provided regarding the X-ray photographing unit 500 as an example of the medical image processing apparatus allowing acquiring of 3-dimensional data in the same manner as, for example, CT, MRI, ultrasonic diagnostic equipment, etc. The X-ray photographing unit 500 comprises a gantry 1, a high-voltage generator 7, an X-ray controller 8, and a gantry/bed controller 9. The gantry 1 comprises a rotating ring 2, an X-ray source (X-ray generating unit) 3, an X-ray filter 4, an X-ray detector 5, a data accumulating unit 11, a pretreating unit 12, and a scan control 501. The X-ray detector 5 is an array type X-ray detector. That is, a channel-wise m row and a slice-wise n column of detecting elements are arranged in a matrix regarding the X-ray detector 5.

The X-ray source 3 and the X-ray detector 5 are installed on the rotating ring 2, facing each other while sandwiching the test object (not illustrated) lay on a sliding bed 6. Respective channels are associated with the respective detecting elements configuring the X-ray detector 5. The X-ray source 3 faces the test object via the X-ray filter 4. When a trigger signal is supplied from the X-ray controller 8, the high-voltage generator 7 activates the X-ray source 3. The high-voltage generator 7 supplies high voltage to the X-ray source 3 at the timing points upon receiving the trigger signals. Thereby, X-rays are generated in the X-ray source 3 and the gantry/bed controller 9 synchronously controls the rotation of the rotating ring 2 of the gantry 1 and the slide of the sliding bed 6.

The scan control 501 configures a central control of all systems and controls the X-ray controller 8, the gantry/bed controller 9, as well as the sliding bed 6 based on conditions for acquiring the projected data specified in advance (hereinafter, may be referred to as the "scanning conditions"). That is, the scan control 501 rotates the rotating ring 2 along a predetermined course around the periphery of the test object while irradiating X-rays from the X-ray source 3. Furthermore, the resolution and resolving power of the projected data are determined based on the scanning conditions determined in advance. In other words, the scanning conditions are determined in advance according to the required resolution and resolving power, while the scan control 501 controls the movement of each part according to the scanning conditions. By means of the resolving power and resolution of the projected data generated according to the scanning conditions (that is, the frame rate), the maximum frame rate and resolution of the reconstructed image data is determined by the reconstruction processing unit 14 mentioned later.

Moreover, the scan control 501 is instructed to change the scanning conditions or stop the processes related to acquiring the projected data (hereinafter, may be referred to as a "scan") from the position analyzing unit 212 of the image processor 20. The image processor 20 and the position analyzing unit 212 are described later. When instructions are given to change the scanning conditions, the scan control 501 changes the scanning conditions to other conditions determined in advance, which are different from the scanning conditions prior to instructions being given. Thereby, for example, before receiving instructions, the resolving power and resolution are lowered in order to acquire rough projected data, and once the instructions are received, the resolving power and resolution are increased more than before receiving instructions in order to obtain the projected data. Thereby, the rough projected data is acquired until instructions are received, and regarding the operation following receiving instructions (that is, the operation requiring attention), the projected data may be acquired at a level in which further careful movements may be observed. Furthermore, the projected data prior to receiving instructions should realize a resolving power and resolution allowing for analysis processing by the image processor 20 mentioned later. That is, if the conditions are satisfied, the scanning conditions may have lower resolving power and resolution settings than the scanning conditions following receiving instructions.

Moreover, when the scanning is instructed to stop, the scan control 501 controls the X-ray controller 8, the gantry/bed controller 9, and the sliding bed 6 to stop scanning. Thereby, the scan control 501 may automatically stop scanning with the instructions as the trigger.

The detected elements configuring the X-ray detector 5 may measure the strength of X-rays generated by the X-ray source 3 regarding both cases of when the test object is interpositioned between the X-ray source 3 and the detected element, and when it is not interpositioned. Accordingly, the respective detected elements measure the intensity of at least one X-ray and output an analog output signal corresponding to the intensity. The signals output from the respective detected elements are classified into columns by time sharing in the data accumulating unit 11 and then read out (that is, successively accumulated).

The data accumulating unit 11 comprises an integrated amplifier and an A/D converter. The electric signals from the respective detected elements comprised in the data accumulating unit 11 are time-shared via a common integrated amplifier and then converted into digital data by the A/D converter. The data accumulating unit 11 outputs to the pretreating unit 12 the signals from the detected elements converted to digital data.

The pretreating unit 12 carries out processes such as correction by sensitivity, etc. on the digital data sent from the data accumulating unit 11, realizing the projected data. The pretreating unit 12 associates the projected data with the column, which is the read-out element of the digital data, which is the generating element thereof, and stores it in the projected data storage 13. The projected data storage 13 is the storage for storing the acquired projected data.

Furthermore, the pretreating unit 12 may supplement identification information indicating the timing point (hereinafter, referred to as a "notification flag") to the projected data when instructions to change the scanning conditions are sent from the scan control 501. Thereby, the reconstruction processing unit 14 functioning in the latter part may specify the timing point in which the scanning condition was changed in the projected data based on the notification flag.

(External Apparatus 51)

The external apparatus 51 is configured from at least any one from among an external photographing unit 511 and a timing point specifying unit 512. The external photographing unit 511 is configured from cameras, etc. that photograph the external appearance (surface portion) of the test object. Moreover, the timing point specifying unit 512 receives specifications regarding the desired timing point from among the series of time widths in which photographing by the X-ray photographing unit 500 was carried out, and supplements the information indicating the timing point to the projected data.

In the present embodiment, the external photographing unit 511 is used as the external apparatus 51. Furthermore, details regarding the timing point specifying unit 512 are explained in later embodiments. The external photographing unit 511 is arranged in a position allowing photographing of the external appearance of the same part as the X-ray photographing unit 500, and images showing the external appearance of the test object are acquired by means of photographing the external appearance of the test object from the position. Hereinafter, the images are referred to as external images. Furthermore, during photographing with the X-ray photographing unit 500, specifically, the external images should be acquired when carrying out analysis processing using the image processing unit 20. Accordingly, acquisition of external images using the external photographing unit 511 may be carried out at the same time as photographing in the X-ray photographing unit 500, or it may be carried out separately from photographing in the X-ray photographing unit 500.

The external photographing unit 511 displays the acquired external images on a display 401 via a display control 30. The display control 30 will be discussed later. Thereby, the operator may confirm the external images displayed on the display 401 and specify external images corresponding to the desired timing points via an operation part 402.

The external photographing unit 511 receives information indicating the external images corresponding to the timing points specified by the operator via the operation part 402. The external photographing unit 511 outputs the external images corresponding to the information to a position analyzing unit 212. The position analyzing unit 212 will be discussed later. Furthermore, at this time, the external photographing unit 511 may notify to the position analyzing unit 212 the positional information indicating the position of itself with respect to the test object together with the external images. Thereby, the position analyzing unit 212 is able to comprehend the photographing position of the external images. Hereinafter, the external photographing unit 511 is explained as a unit that notifies the positional information to the position analyzing unit 212 along with the output of the external images. Furthermore, the positional information is used to specify the position of the viewpoint for projecting the outline objects when comparing the external image with the outline object mentioned later using the position analyzing unit 212.

(Reconstruction Processing Unit 14)

The reconstruction processing unit 14 reads the projected data stored in the projected data storage 13. The reconstruction processing unit 14 uses, for example, a reconstruction algorithm referred to as the Feldkamp method to back project the read project data in order to generate the image data (tomographic image data and volume data). Any method may be adopted to reconstruct the tomographic image data, such as, for example, the 2-dimensional Fourier transformation method, convolution back projection method, etc. The volume data is prepared by interpolation processing the plurality of reconstructed tomographic image data. Any method may be adopted for reconstructing the volume data such as, for example, the cone beam reconstructing method, multi-slice reconstructing method, expanded reconstructing method, etc. Extensive volume data may be reconstructed by means of a volume scan using an X-ray detector with many columns, as mentioned above. Moreover, when carrying out CT examination, the accumulation rate of the detected data is shortened; therefore, the reconstruction time by the reconstruction processing unit 14 is shortened. Accordingly, the real time image data corresponding to the scan may be prepared. Hereinafter, the volume data is referred to as "image data."

In this manner, the reconstruction processing unit 14 carries out reconstruction processing on the read projected data based on the reconstruction conditions determined in advance, and generates or reconstructs image data (that is, volume data) for each timing point based on the reconstructing conditions (that is, the predetermined volume rate). Furthermore, the timing point for reconstructing the image data is synchronized with the timing point for acquiring the projected data (that is, the resolving power related to acquiring the projected data). Specifically, a time lag is present between the timing point in which the projected data for generating the image data from the projected data is acquired and the timing point in which the image data based on the projected data corresponding with the timing is reconstructed. However, the process related to the reconstruction is at a high speed compared to the movement of the test object (for example, the activity of moving the arms and legs), and in the medical image processing apparatus according to the present embodiment, the time lag is at a level in which it is negligible. Furthermore, when the time lag is considered, the timing point for carrying out processing (for example, process of the position analyzing unit 212 mentioned later) based on the reconstructed image data may be adjusted based on the time lag.

Furthermore, the reconstruction processing unit 14 according to the present embodiment first generates the image data for analysis and outputs this to the image processor 20; then, it receives the analysis result from the image processor 20 and generates the image data for display. Details of the image processor 20 are described later. Detailed operations of the reconstruction processing unit 14 are described in the following. Furthermore, the maximum volume rate and the resolution of the reconstructed image data become the resolving power and resolution of the projected data (that is, frame rate). Accordingly, in the medical image processing apparatus according to the present embodiment, the projected data must be acquired under a condition allowing realizing of the volume rate and resolution of the image data for analysis and displaying.

The reconstruction processing unit 14 according to the present embodiment first carries out reconstruction processing with respect to the read projected data based on the reconstruction conditions for analysis determined in advance, and then generates image data for each timing point based on the reconstruction conditions. Furthermore, in the present embodiment, the reconstruction conditions are configured such that the surface portion (that is, the skin) of the test object may be extracted from the projected data. Specifically, regarding the reconstruction conditions, the range of the CT number, which is subject for reconstruction, is adjusted to a level allowing extraction of the surface portion. Thereby, the image data is reconstructed so as to be capable of extracting the surface portion. Moreover, the image data generated based on the reconstruction conditions at this time corresponds with the "first image data." The reconstruction processing unit 14 stores the image data for analysis successively generated for each of the timing points in the image data storage 10. The image data storage 10 is the storage for storing the image data. By means of extracting the surface portion of the test object from such image data, the outline of the test object may be comprehended based on the extracted surface portion. Furthermore, the first image data should have reconstruction conditions allowing for analysis processing using the image processor 20 described later. That is, if the conditions are satisfied, for example, the volume rate of the first image data may be lower than the volume data upon generating the image data for display. Moreover, the resolution of the first image data may be lower than the resolution of the image data for display. The processing load at analysis may be reduced by means of operating in this manner.

(In the Case of Changing the Reconstruction Processing Unit 14 and Frame Rate)

The reconstruction processing unit 14 receives notification of a time width comprising a plurality of timing points from the position analyzing unit 212. The time width corresponds with a part among the series of time widths in which the first image data is generated based on the reconstruction conditions. The reconstruction processing unit 14 carries out reconstruction processing while changing the reconstruction conditions between the notified time width and another time width, and reconstructs the image data for display. The reconstruction conditions may be stored in the reconstruction processing unit 14 in advance, or may be made allowing for an operator to specify via the operation part 402. For example, the reconstruction conditions should be determined such that the volume rate of the specified time width becomes higher than other time widths. Moreover, without limitation to the volume rate, the reconstruction conditions may be determined such that, for example, the resolution of the specified time width becomes higher compared to other time frames. Furthermore, the image data generated based on the reconstruction conditions with respect to the specified time width corresponds to "second projected data." Furthermore, the image data generated based on the reconstruction conditions with respect to the specified time width corresponds with a "second projected data". The reconstruction processing unit 14 stores the image data for analysis successively generated for each of the timing point in the image data storage 10. By means of changing the reconstruction conditions of a part of the time width and generating the image data in this manner, for example, when observing the chronologically operating test object, the image data may be generated at a higher volume rate than other areas regarding one area from among the series of operations (for example, operation of the one are requiring attention). That is, regarding the one area, the medical image may be generated and displayed with higher frame rate than other areas based on the image data chronologically generated in this manner.

Furthermore, regarding other time widths, the first image data generated for analysis may be operated such that it may be additionally used for display. For example, if the observation subject may be specified by the object extracted for analysis and the same applies for the volume data, there is no need to generate the image data for display again. In such cases, the reconstruction processing unit 14 should only reconstruct the image data for display regarding the specified time width. In other words, the reconstruction processing unit 14 should only reconstruct the second image data again as the image data for display. Moreover, the reconstruction processing unit 14 may reconstruct the image data for display regarding only the specified time width (in other words, only the specified time width is subjected for display). The operations should be appropriately changed according to operation. Furthermore, the reconstruction processing unit 14 may supplement different identifying information to the respective image data to distinguish the image data for analysis from the image data for display, thereby distinguishably storing these in the image data storage 10.

(The Reconstruction Processing Unit 14, in the Case of Changing Scanning Conditions and Stopping the Scanning Process)

Furthermore, the X-ray CT scan according to the present embodiment analyzes the reconstructed image data, thereby comprehending the position and angle of each part configuring the observation subject and the relative positional relation (hereinafter, generally referred to as the "positional relations"). Accordingly, the reconstruction processing unit 14 reconstructs the image data for analysis separate from the image data for display. Specifically, the reconstruction processing unit 14 successively reads the acquired projected data from the projected data storage 13 in parallel with the process related to acquiring the projected data using the X-ray photographing unit 500. The reconstruction processing unit 14 carries out reconstruction processing on the read projected data based on the reconstruction conditions determined in advance, thereby generating the image data for analysis for each timing point based on the reconstruction conditions. The reconstruction processing unit 14 stores the image data for analysis generated for each of the timing points in the image data storage 10. Furthermore, the image data generated based on the reconstruction conditions at this time corresponds to the "first image data."

Moreover, the reconstruction processing unit 14 reads the projected data from the projected data storage 13 and carries out reconstruction processing based on the reconstruction conditions determined in advance, thereby generating image data for display for each timing point based on the reconstruction conditions. Furthermore, should the scanning conditions change while acquiring the projected data, the reconstruction processing unit 14 may change the reconstruction conditions before and after changing the scanning conditions and reconstruct the image data for display. In this case, the reconstruction processing unit 14 should specify the timing point with the scanning conditions changed based on the notification flag supplemented in the projected data. By means of operating in this manner, the reconstruction processing unit 14 may increase the volume rate and resolutions of the image data after the scanning conditions have been changed, allowing reconstruction of the image data. Furthermore, hereinafter, the image data generated based on the reconstruction conditions for display may be referred to as "second image data." The reconstruction processing unit 14 stores the image data for display generated for the each timing point in the image data storage 10.

Furthermore, the image data for display does not necessarily need to be operated in parallel with the processing related to acquiring the projected data. For example, the reconstruction processing unit 14 may reconstruct the image for display after a series of projected data has been acquired.

Moreover, the first image data should have the reconstruction conditions under which analyzing processing using the image processing unit 20 mentioned later may be carried out. That is, if the conditions are satisfied, for example, the volume rate of the first image data may be lower than the volume data upon generating the image data for display. Moreover, the resolution of the first image data may be lower than the resolution of the image data for display. The processing load upon analyzing may be reduced by means of operating in this manner.

(Image Processing Unit 20)

The image processing unit 20 includes a configuration extracting unit 21, an image processor 22, and image storage 23.

(Configuration Extracting Unit 21)

The configuration extracting unit 21 includes an object extracting part 211 and a position analyzing unit 212. The configuration extracting unit 21 first reads the first image data reconstructed for analysis for each timing point. Or, the configuration extracting unit 21 successively reads the image data for analysis, which has been successively generated for each timing point using the reconstruction processing unit 14, to the image data storage 10. At this time, operations by the reconstruction processing unit 14 and operations related to reading the image data for analysis to the configuration extracting unit 21 may be synchronized. The configuration extracting unit 21 outputs the respective first image data for each read timing point to the object extracting part 211, providing instructions to extract the object.

The present embodiment explains a case of extracting the object from the first image data and comparing this with the external image, which is the second image showing the flexible sites; however, comparing the first image data itself with the external image may be considered. Moreover, comparing the processed image with the external image may also be considered by carrying out processing without extracting the object from the first image data. Whichever method is used, the first image data of the plurality of timing points is used for comparison with the external image. Thereby, a process is explained regarding specifying the image with timing points shown in the external image, which is the second image data, from among the first image data of the plurality of timing points.

Figure 2A:
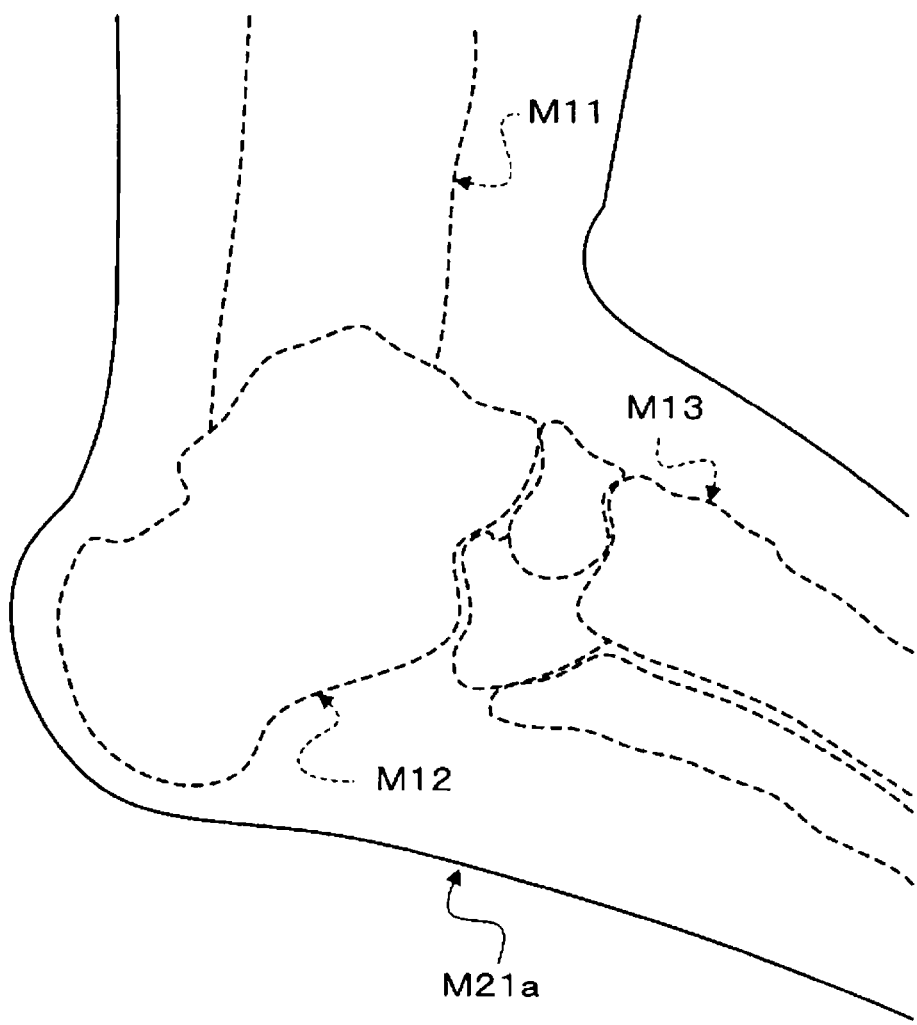
FIG. 2A is a diagram explaining the analysis of the shape based on the surface portion of the test object.
Figure 2B:
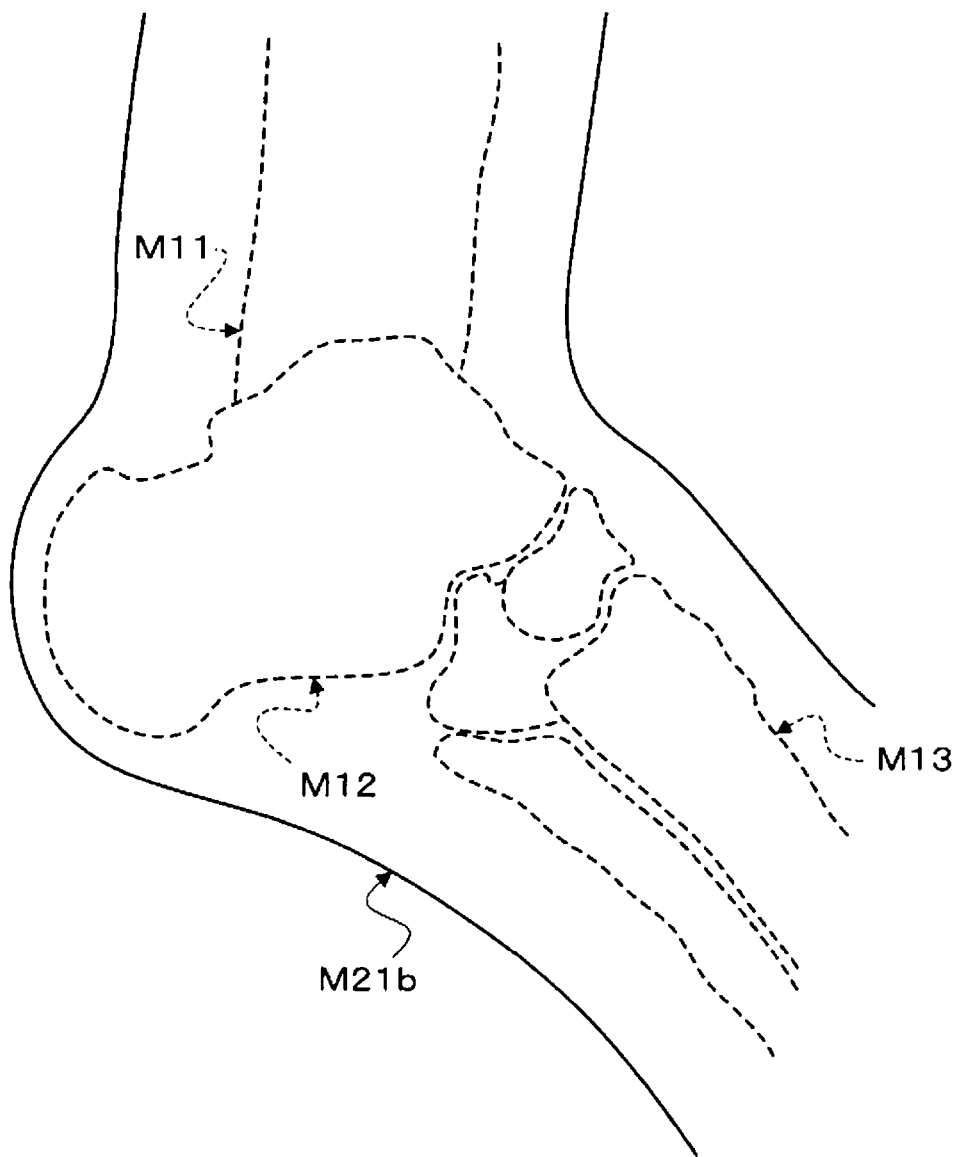
FIG. 2B is a diagram explaining the analysis of the shape based on the surface portion of the test object.

The object extracting part 211 successively receives the first image data for each timing point from the configuration extracting unit 21. The object extracting part 211 according to the present embodiment detects the surface portion of the test objects based on the voxel data in the first image data. The object shows the outline of the test object. The object may be referred to as an outline object. Here, FIG. 2A and FIG. 2B are referred. FIG. 2A and FIG. 2B are diagrams explaining the analysis of the shape based on the surface portion of the test object. FIG. 2A and FIG. 2B show the joints between the upper arm and the lower arm, each corresponding to different timing points. M11 to M13 in FIG. 2A show the bone parts, while M21*a* shows the outline object. Moreover, M11 to M13 in FIG. 2B show the bone parts, and correspond to the M11 to M13 in FIG. 2A. Moreover, M21*b* in FIG. 2B shows the outline object at a timing point different to that of FIG. 2A, and shows a shape different from the outline object M21*a* due to movement of the joints. Furthermore, hereinafter, when the timing point is not particularly specified, the outline object M21*a* and the M21*b* are simply referred to as "outline object M21". Furthermore, the object extracting part 211 corresponds to the "extracting unit."

The object extracting part 211 outputs the information (for example, the information indicating the shape, the position, and the size of the object) showing the external object extracted regarding the respective first image data for each timing point (namely, extracted for each timing point) to the position analyzing unit 212 while relating it with the information indicating the corresponding timing point.

The position analyzing unit 212 receives the information indicating the outline object from the object extracting part 211 for each timing point. Moreover, the position analyzing unit 212 receives the information indicating the external image and the photographing position corresponding to the predetermined timing point from the external photographing unit 511.

Meanwhile, the position analyzing unit 212 analyzes changes in the outline between the respective timing points based on the information indicating the outline object extracted for each timing point. Moreover, the position analyzing unit 212 receives, from the external photographing unit 511, the information indicating the external image and the photographing position corresponding to the predetermined timing points at the desired timing points. When the external images are received, the position analyzing unit 212 specifies the outline object in which the external image and the shape coincide, and with the timing point corresponding to the outline object as the standard, it specifies the timing point controlling operations related to acquiring the projected data of the X-ray photographing unit 500.

Figure 2C:
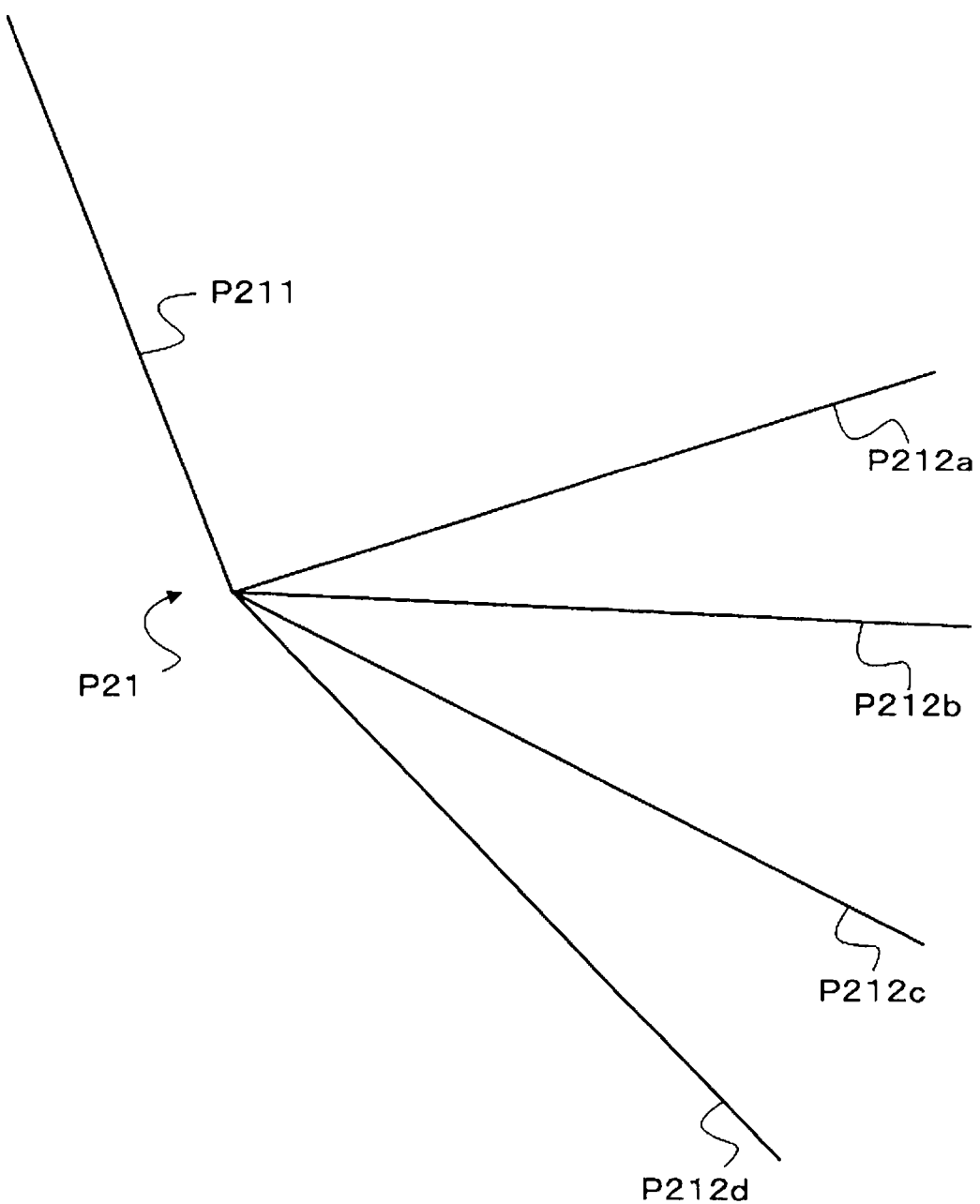
FIG. 2C is a diagram explaining the analysis of the shape based on the surface portion of the test object.

The position analyzing unit 212 specifies the position of the external photographing unit 511 with respect to the test object based on the information indicating the photographing position received from the external photographing unit 511. The position analyzing unit 212 extracts the information indicating the shape of the outline object for each timing point observed from the specified position (hereinafter, referred to as a "shape information") for each of the timing points. As a specific example for extracting the shape, the position analyzing unit 212 should project the respective outline objects with the specified position as the viewpoint and extract a shade formed by the projection as the shape information. Furthermore, a configuration is possible in which the processing is carried out by an image processor 22 mentioned later. Here, FIG. 2C is referred. FIG. 2C is a diagram showing the shape information of the outline object M21 (for example, M21a and M21b) for each timing point in a more schematic manner using lines. P21 in FIG. 2C shows the shape information of the outline object M21. P211 shows the part corresponding to the upper arm (hereinafter, referred to as the "brachial region") in a shape information P21. Furthermore, generally the part corresponding to P211 is extracted for each timing point; however, in the example in FIG. 2C, in order to make the explanation easier to understand, each timing point is shown as being common assuming that the position and angle of the brachial region 211 is unchanged. Moreover, the 212a to P212d shows the part corresponding to the lower arm (hereinafter, referred to as the "antebrachial region"), with each corresponding to different timing points.

The position analyzing unit 212 compares the shape information extracted for each timing point with the external image in terms of their shapes, to calculate the difference therebetween (for example, the number of pixels of areas not overlapping between the two) as the amount of change. Moreover, as an example of another method, the position analyzing unit 212 may extract the axis from both the part corresponding to the upper arm and the part corresponding to the lower arm, and the amount of change may be obtained from the positional relation (for example, angle and angle) of the axes.

Figure 2D:
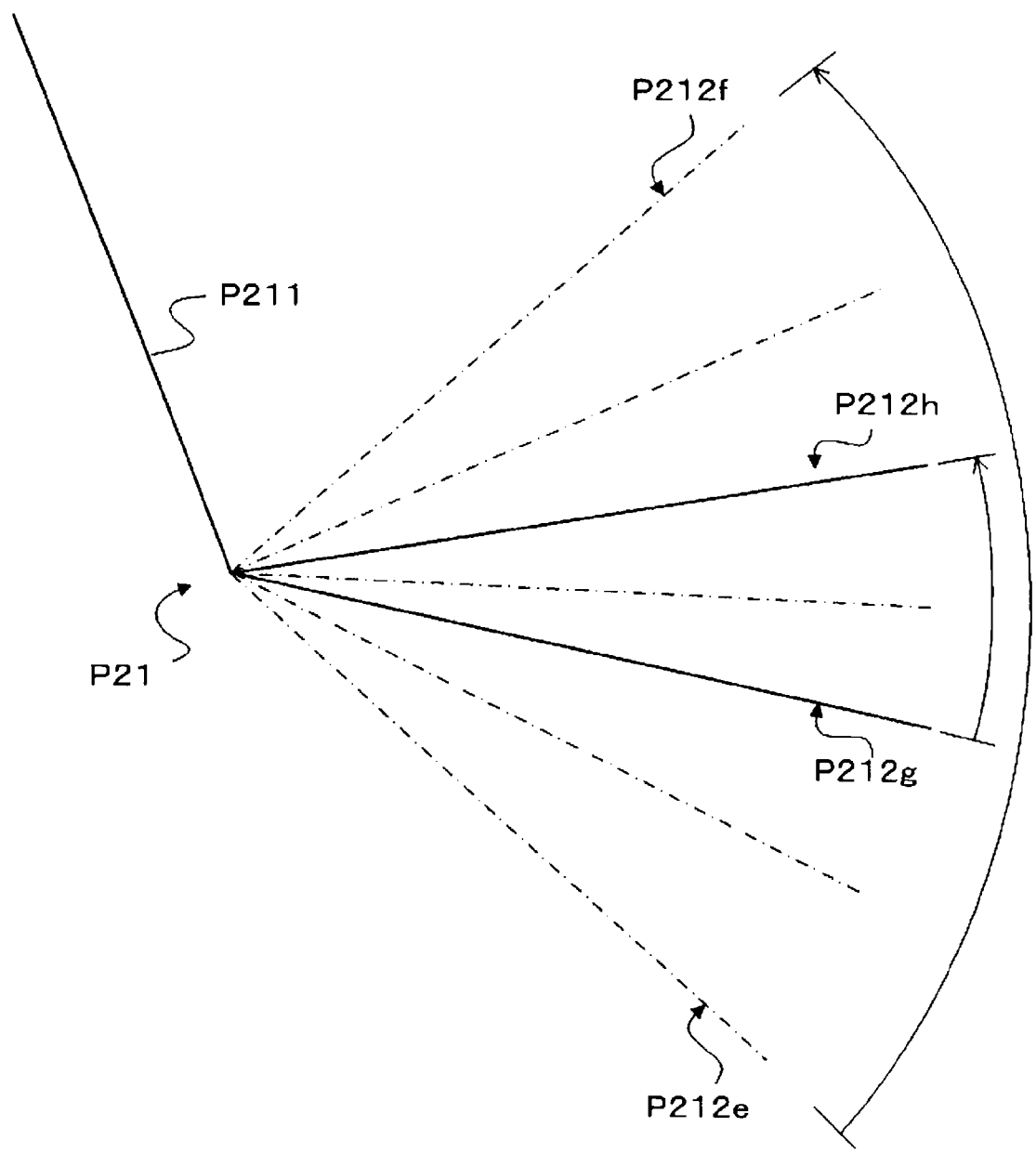
FIG. 2D is a diagram explaining the analysis of the shape based on the surface portion of the test object.

Once the amount of change has been calculated for each timing point, the position analyzing unit 212 determines whether or not the calculated amount of change is within the amount determined in advance (hereinafter, referred to as the "standard value"). The standard value should be determined based on the flexible range requiring attention with the external image as the base point from among the series of movements of the observation subject. Thereby, the position analyzing unit 212 specifies the time width T21 in which the amount of change is shaped from the timing point within the standard value from among the time widths (hereinafter, may be referred to as a "series of time widths") in which the series of outline objects M21 (in other words, the series of first image data) were obtained. Here, FIG. 2D is referred. FIG. 2D shows the time width specified by the position analyzing unit 212. Thereby, the position analyzing unit 212 detects other timing points with the shape of the observation subject changed by within the standard value from among one timing point with the shape of the outline object M21 coinciding with the external image. That is, other timing points are detected with one timing point as the standard.

Furthermore, hereinafter, separate explanations are given regarding the processings of the position analyzing unit 212 which are different between a frame rate changing process or another process to be carried out.

(In the Case of the Position Analyzing Unit 212 and Changing the Frame Rate)

P212e, P212f, and P212g in FIG. 2D respectively show the antebrachial regions P212 when the amount of change between the shape information extracted per timing point and the external image is included within the predetermined range. That is, regarding the time width T21 shaped from the timing point corresponding to the antebrachial region P212f to the timing point corresponding to the antebrachial region P212g, it is exhibited that the amount of change between the shape information extracted for each timing point and the external image is included within the predetermined range. The position analyzing unit 212 specifies the time width T21. Furthermore, T11 and T12 in FIG. 2D show the time widths other than the time width T21 from among the series of time widths. Furthermore, in the explanation hereinafter, the position analyzing unit 212 is explained under the assumption that the time width T21 illustrated in FIG. 2D has been specified.

The position analyzing unit 212 notifies the specified time width T21 to the reconstruction processing unit 14. The reconstruction processing unit 14 changes the reconstruction conditions of the notified time width T21 and other time widths T11 and T12, reconstructing the image data for display for each timing point based on the reconstruction conditions. At this time, the reconstruction processing unit 14 carries out reconstruction process regarding, for example, the time width T21 in which the amount of change between the shape information extracted for each timing point and the external image is included in the predetermined range such that the volume rate becomes higher than the other time widths T11 and T12. Thereby, regarding the time width T21, medical images may be generated and displayed at a frame rate higher than the other time widths T11 and T12. Moreover, regarding the time width T21, the reconstruction processing unit 14 may, for example, carry out reconstruction processing at a higher resolution than the time widths T11 and T12 without limitation to the volume rate. In this manner, the reconstruction processing unit 14 differentiates the time width T21 with other time widths T11 and T12 so as to be capable of reconstructing the image data for display under respectively different reconstruction conditions. The reconstruction processing unit 14 stores the series of reconstructed image data for display in the image data storage 10. Furthermore, the position analyzing unit 212 corresponds to the "analyzing unit."

After shape analysis of the outline objects M21 regarding the series of timing points is finished in this manner and the series of reconstructed image data for display are stored in the image data storage 10, the configuration extracting unit 21 reads these and transfers them to the image processor 22. Furthermore the time widths T11 and T12 may be operated such that the first image data generated for analysis may also be used for display. In this case, the position analyzing unit 212 only reads the second projected data corresponding to the specified time width T21 from the image data storage 10. Then, the position analyzing unit 212 may replace the area corresponding to the time width T21 from among the series of first image data that have already been read for analysis with the read second projected data, and transmit the series of image data to the image processor 22.

(In the Case of the Position Analyzing Unit 212, Changing Scanning Conditions, and Stopping the Scan Processing)

When the position analyzing unit 212 detects other timing points with one timing point as the standard, it instructs the scan control 501 to change the scanning conditions or stop the scan. The scan control 501 receives the instructions and carries out the instructed operation (that is, it changes the scanning conditions or stops the scan). Furthermore, which among changing the scanning conditions and stopping the scan to be instructed should be associated in advance with the information indicating the detected timing points (in other words, the positional relation corresponding to the timing point thereof). This is described with reference to FIG. 2D. FIG. 2D shows the positional relation between the one timing point and other timing points, (i.e. the brachial region P211 and the antebrachial region P212) detected using the position analyzing unit 212.

In the example in FIG. 2D, in order to make the explanation easier to understand, the change in position and angle of the antebrachial region P212 for each timing point are shown under the assumption that the position and angle of the brachial region P211 have not been changed. P212e to P212h in FIG. 2D show the antebrachial regions P212 corresponding to different timing points, respectively. Specifically, the antebrachial region P212e in FIG. 2D corresponds to the timing at which the scan is commenced. Moreover, the antebrachial region P212g shows the timing point at which the external images are received, and the antebrachial region P212h shows the timing point at which the amount of change of the shape becomes the standard value (in the explanation of this example, this is referred to as the "first standard value") with the one timing point as the standard, while the information indicating the timing point is associated with the operation of changing the scanning conditions, Moreover, the antebrachial region P212f shows the timing point at which the amount of change becomes the standard value (in the explanation of this example, this is referred to as the "second standard") that is different from that of the antebrachial region P212h, and the information indicating the timing point is associated with the operation of stopping the scan.

In parallel with photographing with the X-ray photographing unit 500, starting from the timing point corresponding to the antebrachial region P212e, the position analyzing unit 212 successively receives information indicating the outline object M21 extracted from the first image data for each specified timing point from the object extracting part 211. At this point, the position analyzing unit 212 is not required to commence the processing related to the above-mentioned analysis.

The position analyzing unit 212 receives external images from the external photographing unit 511 at the timing point corresponding to the antebrachial region P212h. When external images are received, the position analyzing unit 212 commences analysis processing for detecting the other timing points. Specifically, the position analyzing unit 212 compares shapes of the outline object M21 of the external image and the shape information P21 to successively calculate the amount of change, and determines whether or not the calculated amount of change is more than the standard value (that is, the first standard value or the second standard value).

At the timing point corresponding to the antebrachial region P212h, the amount of change reaches the first standard value. The position analyzing unit 212 detects this and instructs the scan control 501 to change the scanning conditions. Thereby, the X-ray CT system becomes capable of switching operations such as obtaining rough projected data under scanning conditions of low resolving power and resolution until the timing point corresponding to the antebrachial region P212h, and obtaining the projected data in which detailed movements may be observed under scanning conditions of high resolving power and resolution from the timing point onwards.

Moreover, at the timing point corresponding to the antebrachial region P212f, the amount of change reaches the second standard value. The position analyzing unit 212 detects this and instructs the scan control 501 to stop scanning.

The scan control 501 receives the instructions and stops the operation related to acquiring the projected data (that is, the scan). By means of operating in this manner, it becomes possible for the X-ray CT system itself to stop scanning at the timing point at which the amount of change becomes the second standard value or more without the operator having to instruct to stop the scan.

When the second image data reconstructed for display is stored in the image data storage 10, the configuration extracting unit 21 reads this and transfers this to the image processor 22. The first image data generated for analysis may be operated such that it may be additionally used for display. In this case, the position analyzing unit 212 should transfer the image data that has already been read for analysis to the image processor 22.

(Image Processor 22)

The image processor 22 receives the series of image data reconstructed for each specific timing point from the configuration extracting unit 21. The image processor 22 carry out image processing on respective image data for each timing based on the predetermined image processing conditions, in order to generate medical images. The image processor 22 cause the image storage 23 to store the generated medical images and the information indicating a timing point corresponding to image data as a generation base point while relating them with each other. The image storage 23 is storage for storing medical images.

(Display Control 30)

When medical images are generated for a series of timing points, the display control 30 reads a series of medical images stored in the image storage 23. The display control 30 refers to information indicating the timing points supplemented to each read medical image, and generates motion images by arranging the series of medical images along a time series (in the order of timing points). The display control 30 displays the generated motion images on the display 401.

Figure 3A:
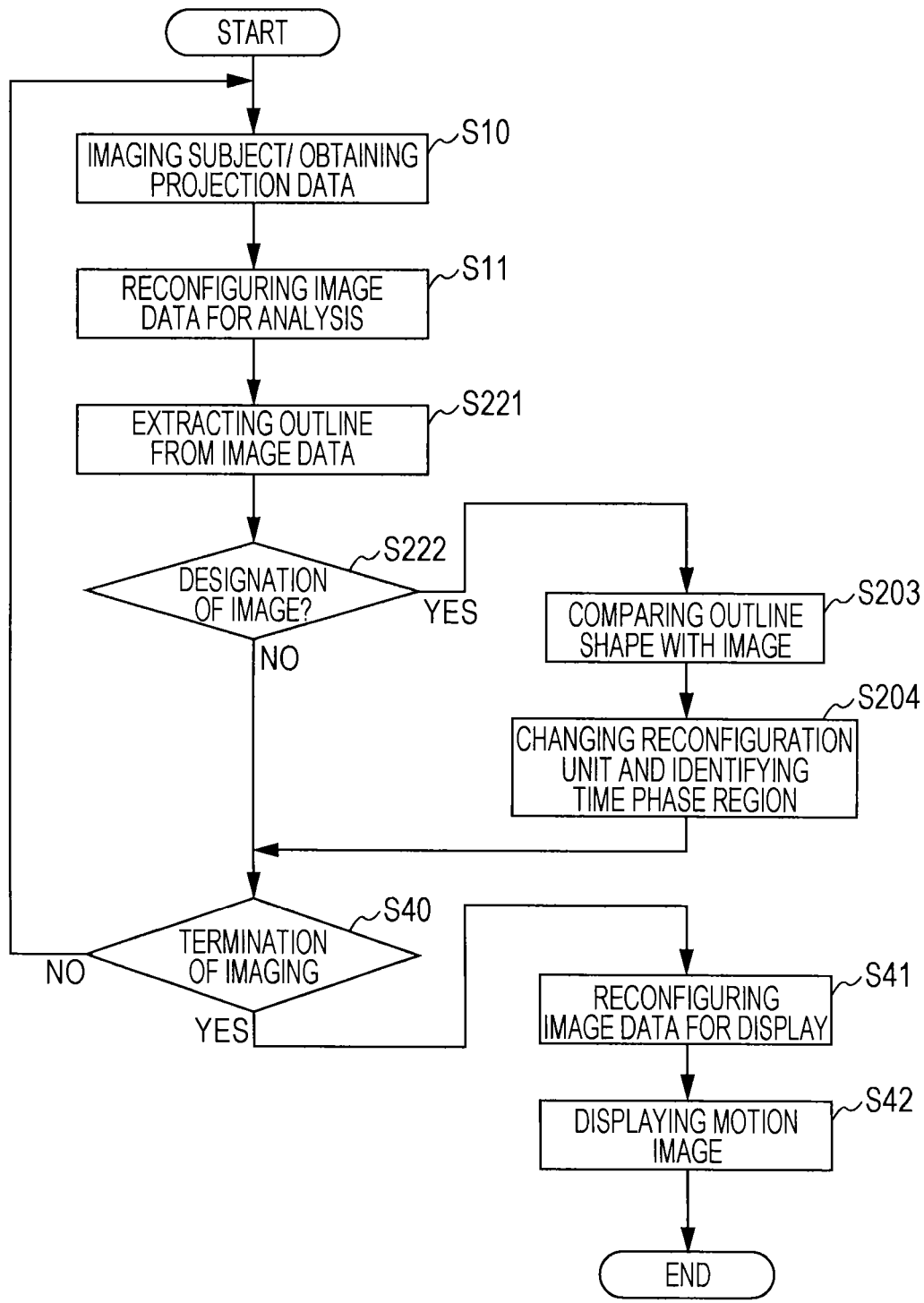
FIG. 3A is a flow chart showing a series of operations of the medical image processing apparatus pertaining to Embodiment 1 (changing the frame rate).
Figure 3B:
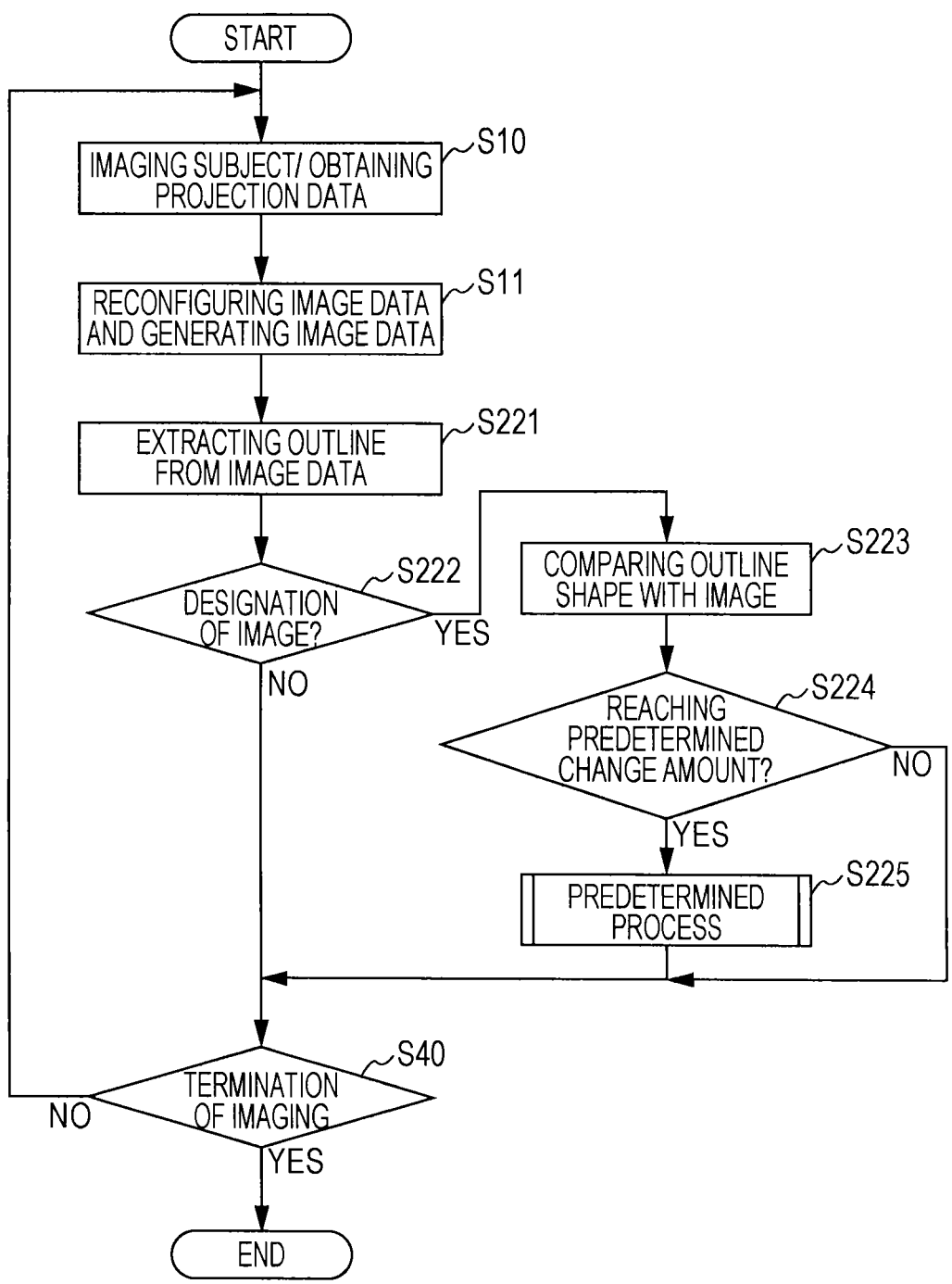
FIG. 3B is a flow chart showing a series of operations of the medical image processing apparatus pertaining to Embodiment 1 (changing scanning conditions, stopping the scan).

Next, the series of operations of the medical image processing apparatus according to the present embodiment is explained with reference to FIGS. 3A and 3B. FIG. 3A and FIG. 3B are flow charts showing a series of operations of the medical image processing apparatus according to the present embodiment.

(Step S10)

When trigger signals are supplied from the X-ray controller 8, the X-ray source 3 is activated by a high-voltage generator 7. The high-voltage generator 7 applies high voltage to the X-ray source 3 at the timing point in which the trigger signals are received. Thereby, X-rays are generated in the X-ray source 3 and the gantry/bed controller 9 synchronously controls the rotation of the rotating ring 2 of the gantry 1 and the slide of the sliding bed 6.

The detected elements configuring the X-ray detector 5 may measure the strength of X-rays generated by the X-ray source 3 regarding both cases when the test object is interpositioned between the X-ray source 3 and the detected element, and when it is not interpositioned. Accordingly, the respective detected elements measure the intensity of at least one X-ray and output an analog output signal corresponding to the intensity. The signals output from the respective detected elements are classified into columns by time sharing in the data accumulating unit 11 and then read (that is, successively accumulated).

The data accumulating unit 11 comprises an integrated amplifier and an A/D converter. The electric signals from the respective detected elements comprised in the data accumulating unit 11 are time-shared via a common integrated amplifier and then converted into digital data by the A/D converter. The data accumulating unit 11 outputs to the pretreating unit 12 the signals from the detected elements converted to digital data.

The pretreating unit 12 carries out processes such as correction by sensitivity, etc. on the digital data sent from the data accumulating unit 11, thereby realizing the projected data. The pretreating unit 12 associates the projected data with the column, which is the read-out element of the digital data, which is the generating element thereof, and stores it in the projected data storage 13.

Moreover, the external photographing unit 511 photographs the external appearance of the test object from the position determined in advance, thereby obtaining the external image showing the external appearance of the test object. The external photographing unit 511 displays the acquired external image on the display 401 via the display control 30. The display control 30 is described later. This allows the operator to confirm the external images displayed on the display 401 and specify the external image corresponding to the desired timing point via an operation part 402.

(Step S11, in the Case of Changing the Frame Rate)

When FIG. 3A is referred, the reconstruction processing unit 14 first carries out reconstruction processing with respect to the read out projected data based on the reconstruction conditions for analysis determined in advance, and then generates the image data for each timing point based on the reconstruction condition. Furthermore, in the present embodiment, the reconstruction conditions are configured such that the surface portion (that is, the skin) of the test object may be extracted from the projected data. The reconstruction processing unit 14 stores the first image data generated for each of the timing point in the image data storage 10.

(Step S11, in the Case of Changing Scanning Conditions and the Scan Stopping Process)

When FIG. 3B is referred, the reconstruction processing unit 14 successively reads the acquired projected data from the projected data storage 13 in parallel with the process related to acquiring the projected data using the X-ray photographing unit 500. The reconstruction processing unit 14 carries out reconstruction processing on the read projected data based on the reconstruction conditions for analysis determined in advance, thereby generating the image data for analysis for each timing point based on the reconstruction conditions. The reconstruction processing unit 14 stores the image data for analysis generated for each of the timing points in the image data storage 10.

(Step S221)

In the case of changing the scanning conditions and the scan stopping process, the configuration extracting unit 21 successively reads the image data for analysis, which is successively generated by the reconstruction processing unit 14 at each timing point and stored in the image data storage 10, from the image data storage 10. At this time, operations by the reconstruction processing unit 14 and operations related to reading the image data for analysis to the configuration extracting unit 21 may be synchronized. The configuration extracting unit 21 successively outputs the first image for each read timing point to the object extracting part 211, and instructs to extract the object from the first image data.

The object extracting part 211 successively receives image data for each timing point from the configuration extracting unit 21. The object extracting part 211 according to the present embodiment detects the surface portion of test objects based on the voxel data in this image data, and extracts the object within the range shaped from the detected surface portion. The object shows the outline of the test object. The object may be referred to as an outline object. Here, FIG. 2A and FIG. 2B are referred. FIG. 2A and FIG. 2B are diagrams explaining the analysis of the shape based on the surface portion of the test object. FIG. 2A and FIG. 2B show the joints between the upper arm and the lower arm, each corresponding to different timing points. M11 to M13 in FIG. 2A show the bone parts, while M21a shows the outline object. Moreover, M11 to M13 in FIG. 2B show the bone parts, and correspond to the M11 to M13 in FIG. 2A. Moreover, M21b in FIG. 2B shows the outline object at a timing point different to that of FIG. 2A, and shows a shape different from the outline object M21a due to movement of the joints The object extracting part 211 outputs the information (for example, the information indicating the shape, the position, and the size of the object) showing the external object extracted regarding the respective first image data for each timing point (namely, extracted for each timing point) to the position analyzing unit 212 while relating it with the information indicating the corresponding timing point.

(Step S222)

The external photographing unit 511 receives information indicating external images corresponding to the desired timing point specified by the operator via the operation part 402 at the desired timing point (Step S222, Y). The external photographing unit 511 outputs the external image corresponding to the information to the position analyzing unit 212. Furthermore, the medical image processing apparatus according to the present embodiment continues the series of operations until it receives the specifications of the information indicating the external image (Step S222, N), as long as it is instructed to stop photographing (Step S40, N).

Hereinafter, separate explanations are given regarding the case of changing the frame rate illustrated in FIG. 3A and the case of changing the scanning conditions illustrated in FIG. 3B because the processing thereof differs when stopping the scan.

(In the Case of Changing the Frame Rate)
(Step S203)

The position analyzing unit 212 receives information indicating the outline object from the object extracting part 211 for each timing point. Moreover, the position analyzing unit 212 receives information indicating the external image corresponding to the specified timing points and the photographing position from the external photographing unit 511.

The position analyzing unit 212 specifies the position of the external photographing unit 511 with respect to the test object based on the information indicating the photographing position received from the external photographing unit 511. The position analyzing unit 212 extracts the information indicating the shape of the outline object for each timing point observed from the specified position (hereinafter, referred to as a "shape information") for each of the timing points. As a specific example for extracting the shape, the position analyzing unit 212 should project the respective outline objects with a specified position as the viewpoint. Furthermore, a configuration is possible in which the processing is carried out by an image processor 22 mentioned later. Here, FIG. 2C is referred. FIG. 2C shows the shape information of the outline object M21 (for example, M21a and M21b) for each timing point in a more schematic manner using lines. P21 in FIG. 2C shows the shape information of the outline object M21. P211 shows the part corresponding to the upper arm (hereinafter, referred to as the "brachial region") in the shape information P21. Furthermore, generally, the part corresponding to P211 is extracted for or each timing point; however, in the example in FIG. 2C, in order to make the explanation easier to understand, each timing point is shown as being common assuming that the position and angle of the brachial region 211 are unchanged. Moreover, the 212a to P212d shows the part corresponding to the lower arm (hereinafter, referred to as the "antebrachial region"), with each corresponding to different timing points.

The position analyzing unit 212 compares the shape information extracted for each timing point with the external image in terms of shapes, and calculates the difference therebetween (for example, the number of pixels of parts not overlapping between objects) as the amount of change. Moreover, as an example of another method, the position analyzing unit 212 may extract axes from the part corresponding to the upper arm and the part corresponding to the lower arm, respectively, thereby obtaining the amount of change from the positional relation (for example, angle and angle) of the axes.

(Step S204)

Once the amount of change has been calculated for each timing point, the position analyzing unit 212 determines whether or not the calculated amount of change is within the amount determined in advance (hereinafter, referred to as the "standard value"). Thereby, the position analyzing unit 212 specifies the time width T21 in which the amount of change is shaped from the timing point within the standard value from among the time widths (hereinafter, may be referred to as the "series of time width") in which the series of outline objects M21 (in other words, the series of first image data) were obtained. Here, FIG. 2D is referred. FIG. 2D explains the time width specified by the position analyzing unit 212.

The planes P212e, P212f, and P212g in FIG. 2D respectively show the antebrachial regions P212 when the amount of change between the shape information extracted per timing point and the external image is included within the predetermined range. That is, during the time width T21 shaped from the timing point corresponding to the antebrachial region P212f to the timing point corresponding to the antebrachial region P212g, it is exhibited that the amount of change between the shape information extracted for each timing point and the external image is included within the predetermined range. The position analyzing unit 212 specifies the time width T21. Furthermore, T11 and T12 in FIG. 2D show the time widths other than the time width T21 from among the series of time widths. The position analyzing unit 212 notifies the specified time width T21 to the reconstruction processing unit 14.

(Step S40)

Furthermore, the X-ray photographing unit 500 and the medical image processing apparatus according to the present embodiment carry out the abovementioned series of processes as long as they are not instructed to stop photographing by the operator (Step S40, N). Once it is instructed by the operator to terminate photographing (Step S40, Y), it transits to the next process.

(Step S41)

The reconstruction processing unit 14 receives notification of the time width comprising a plurality of timing points (that is, time width) from the position analyzing unit 212. The time width corresponds to a part from among the series of time widths at which the first image data was generated based on the reconstruction conditions. The reconstruction processing unit 14 carries out reconstruction processing while changing the reconstruction conditions between the notified time width and another time width, and reconstructs the image data for display. The reconstruction conditions may be stored in the reconstruction processing unit 14 in advance, or may be made allowing for an operator to specify via the operation part 402. Moreover, the reconstruction conditions should be determined such that, for example, the volume rate of the specified time width becomes higher than other time widths. Furthermore, the image data generated based on the reconstruction conditions with respect to the specified time width corresponds to the "second image data". The reconstruction processing unit 14 stores the image data for display generated for each of the timing point in the image data storage 10.

(Step S42)

When the shape analysis of the outline object M21 regarding the series of timing points terminates in this manner and the series of image data reconstructed for display is stored in the image data storage 10, the configuration extracting unit 21 reads these and transfers them to the image processor 22. Furthermore as to the time widths T11 and T12 it is also possible to use for display the first image data generated for analysis. In this case, the position analyzing unit 212 only reads the second projected data corresponding to the specified time width T21 from the image data storage 10. Then, the position analyzing unit 212 should replace the area corresponding to the time width T21 from among the series of first image data that have already been read for analysis with the read second projected data, and transmit the series of image data to the image processor 22.

The image processor 22 receives the series of image data reconstructed for each specific timing point from the configuration extracting unit 21. The image processor 22 carries out image processing on each image data for each timing point based on the image processing conditions determined in advance, thereby generating the respective medical images. The image processor 22 causes the image storage 23 to store the generated medical images and the information indicating the timing point corresponding to image data as a generation base point while relating them with each other.

(Display Control 30)

When medical images are generated for a series of timing points, the display control 30 reads a series of medical images stored in the image storage 23. The display control 30 refers to information indicating the timing points supplemented to each read medical images, and generates motion images by arranging the series of medical images along a time series. The display control 30 displays the generated motion images on the display 401.

Furthermore, in the above, the image data for display was generated after the series of photographing had been completed (that is, acquiring the projected data using the X-ray photographing unit 500); however, once analysis using the position analyzing unit 212 is completed, the generation of image data for display may be commenced. Accordingly, the series of photographing, generation of the image data for display, and the processing related to the generation as well as display of the medical images accompanying this may be carried out in parallel.

Furthermore, the above explained is an example in which the reconstruction of image data is operated using the medical image processing apparatus by synchronizing with the photographing by the X-ray photographing unit 500 (that is, acquiring the projected data); however, the X-ray photographing unit 500 and the medical image processing apparatus may be asynchronously operated (that is, at different timing points). In this case, the operations related to Step S10 are carried out using the X-ray photographing unit 500 and the projected data is acquired in advance. Subsequently, the medical image processing apparatus should be caused to carry out the series of operations shown in steps S11, S221 to S222, S203 to S204, S41, and S42.

As mentioned above, the medical image processing apparatus according to the present embodiment analyzes the change in positional relation of at least two or more parts configuring the flexible sites such as joints, etc. from the change in the outline of the test object. On this basis, with respect to the external image determined in advance, the medical image processing apparatus specifies the time width in which the amount of change of the outline is included within the predetermined range, carries out reconstruction processing within the time width and the other time widths by changing the reconstruction conditions, and reconstructs the image data for display. Thereby, the medical image processing apparatus according to the present embodiment becomes capable of displaying the time width in which the positional relation of two or more parts are included within the predetermined range at a higher frame rate than other time widths.
(In the Case of Changing the Scanning Conditions and the Scan Stopping Process)
(Step S223)

The position analyzing unit 212 successively receives information indicating the outline object extracted from the object extracting part 211 for each timing point. The position analyzing unit 212 analyzes the change in the outline between each of the timing points based on the information. Moreover, the position analyzing unit 212 receives the external image corresponding to the predetermined timing points and the information indicating the photographing position from the external photographing unit 511 at desired timing points. Once the external images are received, the position analyzing unit 212 specifies the outline object in which the shape thereof coincides with the external image, and with the timing points corresponding to the outline object as the standard, it specifies the timing point controlling the operations related to acquiring the projected data of the X-ray photographing unit 500. An example of a specific method thereof will be described below.

The position analyzing unit 212 specifies the position of the external photographing unit 511 with respect to the test object based on the information when it receives information indicating a photographing position. The position analyzing unit 212 extracts the information indicating the shape of the outline object successively received for each timing point observed from the specified position (hereinafter, referred to as "shape information"). As a specific example for extracting the shape, the position analyzing unit 212 should project the respective outline objects with the specified position as the viewpoint, and extract the projection as the shape information. Furthermore, a configuration is possible in which the processing is carried out by an image processor 22 mentioned later. Here, FIG. 2C is referred. FIG. 2C depicts shape information of outline objects M21 (e.g. M21a amd M21b) by lines. P21 in FIG. 2C shows the shape information of the outline object M21. P211 shows the part corresponding to the upper arm (hereinafter, referred to as the "brachial region") in the shape information P21. Furthermore, generally, the part corresponding to P211 is extracted for each timing point; however, in the example in FIG. 2C, in order to make the explanation easier to understand, each timing point is shown as being common assuming that the position and angle of the brachial region 211 is unchanged. Moreover, the 212a to P212d shows the part corresponding to the lower arm (hereinafter, referred to as the "antebrachial region"), with each corresponding to different timing points.

The position analyzing unit 212 compares the shape information extracted for each timing point with the external image in terms of shapes, and calculates the difference therebetween (for example, the number of pixels of parts not overlapping between objects) as the amount of change. Alternatively, the position analyzing unit 212 may extract axes from the part corresponding to the upper arm and the part corresponding to the lower arm, respectively, thereby obtaining the amount of change from the positional relation (for example, angle and angle) of the axes.
(Step S224)

Once the amount of change has been calculated, the position analyzing unit 212 determines whether or not the calculated amount of change is within the amount determined in advance (hereinafter, referred to as the "standard value"). The standard value should be determined based on the flexible range requiring attention with the external image as the base point from among the series of movements of the observation subject. Thereby, the position analyzing unit 212 detects other timing points with the shape of the observation subject changed by within the standard value from among one timing point with the shape of the outline object M21 coinciding with the external image. That is, other timing points are detected with one timing point as the standard.
(Step S225)

When the position analyzing unit 212 detects other timing points with one timing point as the standard (Step S224, Y), it instructs the scan control 501 to change the scanning conditions or to stop the scan. The scan control 501 receives the instructions and carries out the instructed operation (that is, it changes the scanning condition or stops the scan). Furthermore, during the time in which the other timing points are not detected (Step S224, N), the position analyzing unit 212 does not give instructions to the scan control 501 and transits to the next process.
(Step S13)

Furthermore, the X-ray CT system according to the present embodiment carries out the series of processes unless instructions to stop photographing are given by the operator (Step S13, N). When instructions to stop photographing are given by the operator (Step S13, Y), the X-ray CT system according to the present embodiment terminates the process related to acquiring the projected data together with terminating the analysis processing for controlling this.

As described above, the X-ray CT system according to the present embodiment analyzes changes in the positional relationship of at least two or more sites constructing flexible sites such as a joint in accordance with the bones corresponding to these sites. Moreover, the X-ray CT system detects the timing point at which the amount of change in the outline became the standard value or more with respect to the external image specified in advance, to control the operation related to acquiring the projected data based on this timing point (that is, it changes the scanning conditions or stops scanning). Thereby, in the X-ray CT system according to the present embodiment, the X-ray CT system itself can automatically control the operation for acquiring projected data without the operator when the positional relationship of two or more sites satisfies predetermined conditions.
(Embodiment 2)

Next, the medical image processing apparatus according to Embodiment 2 is explained. In the medical image processing apparatus according to Embodiment 1, the external photographing unit 511 was used as the external apparatus 51 to obtain the external images and the time width T21 that changes the reconstruction conditions and the timing point controlling the processing related to acquiring the projected data were specified, with external images corresponding to specified timing points as the standard. In the medical image processing apparatus according to the present embodiment, the timing point specifying unit 512 is used as the external apparatus 51 to receive specifications at the desired timing point from among the series of timing points at which photographing by the X-ray photographing unit 500 was carried out, and specifies the time width T21 that changes the reconstruction conditions and the timing points controlling the processes related to acquiring the projected data with the timing points as the standard.

The medical image processing apparatus according to the present embodiment is explained in the following focusing on the parts different from Embodiment 1.

The timing point specifying unit 512 receives specifications regarding the desired timing point from among the series of time widths in which photographing by the X-ray photographing unit 500 was carried out, and supplements the information indicating the timing point to the projected data. Specifically, as an example, when a reaction of the test object (for example, uttering from the test object) is detected from a microphone detecting the voice of the test object, the timing point specifying unit 512 receives notifications showing this. When notification is received from the microphone, the timing point specifying unit 512 supplements identification information indicating the timing point that receives the notification (hereinafter, referred to as a "notification flag") to the projected data acquired using the X-ray photographing unit 500. Moreover, without limitation to microphones, when specific reactions are detected from the test object using apparatuses monitoring reactions of the test object, such as, for example, cameras, heart rate meters, etc., the timing point specifying unit may operate by receiving notifications showing these reactions. Moreover, the timing point specifying unit 512 may also receive the specifications of the timing point from the operator via the operation part 402. For example, during photographing by the X-ray photographing unit 500, the operator gives instructions to the timing point specifying unit 512 via the operation part 402 at the desired timing point. The timing point specifying unit 512 should receive instructions by the operator from the operation part 402, and supplement the notification flag showing the timing points that received the instructions to the projected data. Moreover, a configuration may be taken in which the scan control 501 controls the timing point specifying unit 512 together with photographing by the X-ray photographing unit 500.

Hereinafter, separate explanations are provided because the processing thereof differs in the case of changing the frame rate, changing the scanning conditions, and stopping the scanning.

(In the Case of Changing the Frame Rate)

The reconstruction processing unit 14 reads the projected data stored in the projected data storage 13.

The reconstruction processing unit 14 first carries out reconstruction processing with respect to the read projected data based on the reconstruction conditions for analysis determined in advance, and then generates the image data for each timing point based on the reconstruction conditions. Furthermore, in the present embodiment, the reconstruction conditions are configured such that the surface portion (that is, the skin) of the test object may be extracted from the projected data. Thereby, the image data is reconstructed allowing extraction of the surface portion. Moreover, when reconstructing the image data with respect to the timing points including the timing point shown by the notification flag supplemented to the projected data, the reconstruction processing unit 14 supplements to the image data the identification information for differentiating with other image data (hereinafter, referred to as a "notification flag"). Furthermore, the image data generated based on the reconstruction conditions at this time corresponds with the "first image data." The reconstruction processing unit 14 stores the image data for analysis successively generated for each of the timing points in the image data storage 10.

Furthermore, the processing related to reconstruction of the image data for display of the reconstruction processing unit 14 related to the present embodiment is the same as the operation of the reconstruction processing unit 14 related to Embodiment 1. That is, the reconstruction processing unit 14 receives notification of the time width T21 comprising the plurality of timing points from the position analyzing unit 212. The reconstruction processing unit 14 carries out reconstruction processing while changing the reconstruction conditions between the notified time width T21 and other time widths T11 and T12, reconstructing the image data for display, and stores these in the image data storage 10.

Moreover, the medical image processing apparatus according to the present embodiment may be operated such that processing related to analysis is not carried out when the notification flag is not supplemented in the projected data. In this case, the reconstruction processing unit 14 should only reconstruct the image data for display based on the reconstruction conditions for display determined in advance.

The configuration extracting unit 21 first reads the first image data reconstructed for analysis for each timing point. The configuration extracting unit 21 outputs the respective first image data for each read timing point to the object extracting part 211, providing instructions to extract the object. The operation of the configuration extracting unit 21 is the same as Embodiment 1.

The object extracting part 211 receives the first image data for each timing point from the configuration extracting unit 21. The object extracting part 211 detects the surface portion of test objects based on the voxel data in this image data, and extracts the outline object M21 within the range shaped from the extracted surface portion. Moreover, when the notification flag is supplemented to the first image data, the object extracting part 211 associates the notification flag to the information indicating the outline object M21 extracted from the image data. The object extracting part 211 associates the information indicating the outline object M21 extracted regarding each first image data at each timing point with the information indicating the corresponding timing point, and outputs this to the position analyzing unit 212.

The position analyzing unit 212 receives the information indicating the outline object M21 from the object extracting part 211 for each timing point. The position analyzing unit 212 analyzes the change in outline along the time series based on the information. An example of a specific method thereof will be described below.

First, the position analyzing unit 212 specifies an object in which the outline object M21 supplemented with the notification flag becomes the standard from among the outline objects M21 for each timing point. Furthermore, hereinafter, the outline object that becomes the standard may be referred to as the "standard object."

Once the standard object has been specified, the position analyzing unit 212 compares the standard object with the outline object for each timing point, and calculates the amount of change between the objects for each timing point. Specifically, the position analyzing unit 212 compares the shape of the two objects, and calculates the difference thereof (for example, the number of pixels of areas not overlapping between the two) as the amount of change. Moreover, as an example of another method, the position analyzing unit 212 may extract axes from the part corresponding to the upper arm and the part corresponding to the lower arm, respectively, and the amount of change may be obtained based on the positional relation (for example, angle and angle) of the axis.

Once the amount of change has been calculated for each timing point, the position analyzing unit 212 determines whether or not the calculated amount of change is within the amount determined in advance (hereinafter, referred to as the "standard value"), and specifies the time width shaped from the timing points in which the amount of change is within the standard. The standard value should be determined based on, for example, the flexible range requiring attention with the external image as the base point from among the series of movements of the observation subject. Thereby, by comparing the standard object with the outline object in terms of shapes, the position analyzing unit 212 analyzes the positional relation of each part configuring the test object and specifies the time width that satisfies the predetermined conditions. Furthermore, the time width corresponds to the time width T21 in Embodiment 1 (refer to FIG. 2D), while the others correspond to the time widths T11 and T12. Hereinafter, the position analyzing unit 212 will be described assuming that this time width T21 is identified. The position analyzing unit 212 notifies the reconstruction processing unit 14 of the identified time width T21.

Further, the following processing is the same as the first embodiment. In other words, the reconstruction processing unit 14 carries out reconstruction processing while changing the reconstruction conditions in the notified time width T21, and other time widths T11 and T12, then reconstructs image data for display for each timing point based on the reconstruction conditions. The reconstruction processing unit 14 causes the image data storage 10 to store the reconstructed series of image data for display. The image processor 22 carries out image processing on this image data and generates medical images, storing these medical images in the image storage 23 as related to the information indicating a corresponding timing point. The display controller 30 reads these medical images from the image storage 23 and arranges these medical images along a time sequence to cause the display 401 to display them as motion images.

(In the Case of Changing the Scanning Conditions and the Scan Stopping Process)

The X-ray CT system according to the present embodiment analyzes the reconstructed image data, thereby comprehending the position and angle of each part configuring an observation subject as well as the relative positional relation thereof (hereinafter, this is generally simply referred to as the "positional relation"). Therefore, the reconstruction processing unit 14 reconstructs the image data for analysis separately from the image data for display. Specifically, the reconstruction processing unit 14 successively reads the acquired projected data from the projected data storage 13 in parallel with the processing related to acquiring the projected data using the X-ray photographing unit 500. The reconstruction processing unit 14 carries out reconstruction processing on the read projected data based on the reconstruction conditions for analysis determined in advance, thereby generating the image data for analysis for each timing point based on the reconstruction conditions.

In the present embodiment, the reconstruction conditions for reconstructing the image data for analysis are configured such that the bones in the test object may be extracted from the projected data. Specifically, the reconstruction conditions are adjusted to a level allowing the layer surface to extract the range of CT number, which is subjected to reconstruction. Thereby, the image data is reconfigured such that the surface portion may be extracted. Moreover, when reconstructing the image data with respect to the timing points including the timing point shown by the notification flag supplemented to the projected data, the reconstruction processing unit 14 supplements to the image data the identification information for differentiating with other image data (hereinafter, referred to as a "notification flag"). Furthermore, the image data generated based on the reconstruction conditions at this time corresponds with the "first image data." The reconstruction processing unit 14 stores the image data for analysis successively generated for each of the timing points in the image data storage 10. By means of extracting the surface portion of the object from such image data, the external appearance of the test object may be confirmed based on the extracted surface portion. In the present embodiment, the change in the outline of the test object along the time series is analyzed based on the surface portion of the test object reconstructed in this manner, and the timing points controlling the operations related to acquiring the projected data are specified by whether or not the outline satisfies the predetermined conditions.

Furthermore, the processing related to reconstruction of the image data for display of the reconstruction processing unit 14 according to the present embodiment is the same as the operation of the reconstruction processing unit 14 according to Embodiment 1. That is, the reconstruction processing unit 14 reads the projected data from the projected data storage 13, and carries out reconstruction processing based on the reconstruction conditions for display determined in advance, thereby generating the image data for display for each timing point based on the reconstruction conditions. Furthermore, hereinafter, the image data generated based on the reconstruction conditions for display may be referred to as "second image data." The reconstruction processing unit 14 stores the image data for display generated for the each timing point in the image data storage 10.

Furthermore, the image data for display does not necessarily need to be operated in parallel with the processing related to acquiring the projected data. For example, the reconstruction processing unit 14 may reconstruct the image for display after a series of projected data has been acquired. The operation is also the same as in Embodiment 1.

The configuration extracting unit 21 successively reads the image data for analysis, which is successively generated by the reconstruction processing unit 14 at each timing point and stored in the image data storage 10, from the image data storage 10. At this time, operations by the reconstruction processing unit 14 and operations related to reading the image data for analysis to the configuration extracting part 21 may be synchronized. The configuration extracting part 21 successively outputs the first image for each read timing points to the object extracting part 211, and instructs extraction of the object from the first image data. The operation of the configuration extracting unit 21 is the same as Embodiment 1

The object extracting part 211 successively receives image data for each timing point from the configuration extracting part 21. The object extracting part 211 according to the present embodiment detects the surface portion of the test object based on voxel data in this first image data, and extracts the object in the range formed by the detected surface portion. This object represents the outline of the test object. Moreover, when the notification flag is supplemented to the first image data, the object extracting part 211 associates the notification flag to the information indicating the outline object M21 extracted from the image data. The object extracting part 211 associates the information indicating the outline object M21 extracted regarding each first image data at each timing point with the information indicating the corresponding timing point, and outputs this to the position analyzing unit 212. The position analyzing unit 212 successively receives the information indicating the outline object extracted for each timing point from the object extracting part 211. The position analyzing unit 212 analyzes the change in outline along the time series based on the information.

The position analyzing unit 212 specifies the outline object supplemented with the notification flag from among the successively received outline objects, and specifies the timing point controlling the operations related to acquiring the projected data with the timing point corresponding to the outline object as the standard it specifies the timing point controlling the operations related to acquiring the projected data of the X-ray photographing unit 500. An example of a specific method thereof will be described below.

The position analyzing unit 212 confirms whether or not the notification flag is supplemented to each outline object successively received for each timing point, and detects the outline object supplemented with the notification flag. When the external object supplemented with the notification flag is detected, the position analyzing unit 212 specifies the standard object of the outline object. Furthermore, hereinafter, the outline object that becomes the standard may be referred to as the "standard object."

Once the standard object has been specified, the position analyzing unit 212 compares the standard object with the outline object for each timing point, and calculates the amount of change between the objects for each timing point. Specifically, the position analyzing unit 212 compares the shape of the two objects, and calculates the difference therebetween (for example, the number of pixels of areas not overlapping between the two) as the amount of change. Moreover, as an example of another method, the position analyzing unit 212 may extract axes from the part corresponding to the upper arm and the part corresponding to the lower arm, respectively, and the amount of change may be obtained based on the positional relation (for example, angle and angle) of the axes.

Once the amount of change has been calculated, the position analyzing unit 212 determines whether or not the calculated amount of change is more than the amount determined in advance (hereinafter, referred to as the "standard value"). The standard value should be determined based on, for example, the flexible range requiring attention with the timing points corresponding to the standard object as the base point from among the series of movements of the observation subject. Thereby, the position analyzing unit 212 detects other timing points with the shape of the observation subject changed by within the standard value from among one timing point with the shape of the outline object M21 coinciding with the standard object. That is, other timing points are detected with one timing point as the standard.

When the position analyzing unit 212 detects other timing points with one timing point as the standard, it instructs the scan control 501 to change the scanning conditions or stop the scan. The scan control 501 receives the instructions and carries out the instructed operation (that is, it changes the scanning conditions or stops the scan). Furthermore, which among changing the scanning conditions and stopping the scan to be instructed should be associated in advance with the information indicating the detected timing points (in other words, the positional relation corresponding to the timing point thereof).

Furthermore, the operations hereinafter are the same as in Embodiment 1. That is, when the second image data reconstructed for display is stored in the image data storage 10, the configuration extracting unit 21 reads this and transfers it to the image processor 22. Furthermore, the first image data generated for analysis may be operated such that it may be additionally used for display. In this case, the position analyzing unit 212 should transfer the image data for analysis that has already been read to the image processor 22. The image processor 22 carries out image processing on the image data to generate medical images, and stores them in the image storage 23 while associating them with the information indicating the corresponding timing points. The display control 30 reads the medical images from the image storage 23 and displays motion images on the display 401 by arranging them along a time series.

(Commonalities in the Case of Changing the Frame Rate, Changing the Scanning Conditions, and the Scan Stopping Process)

Figure 4A:
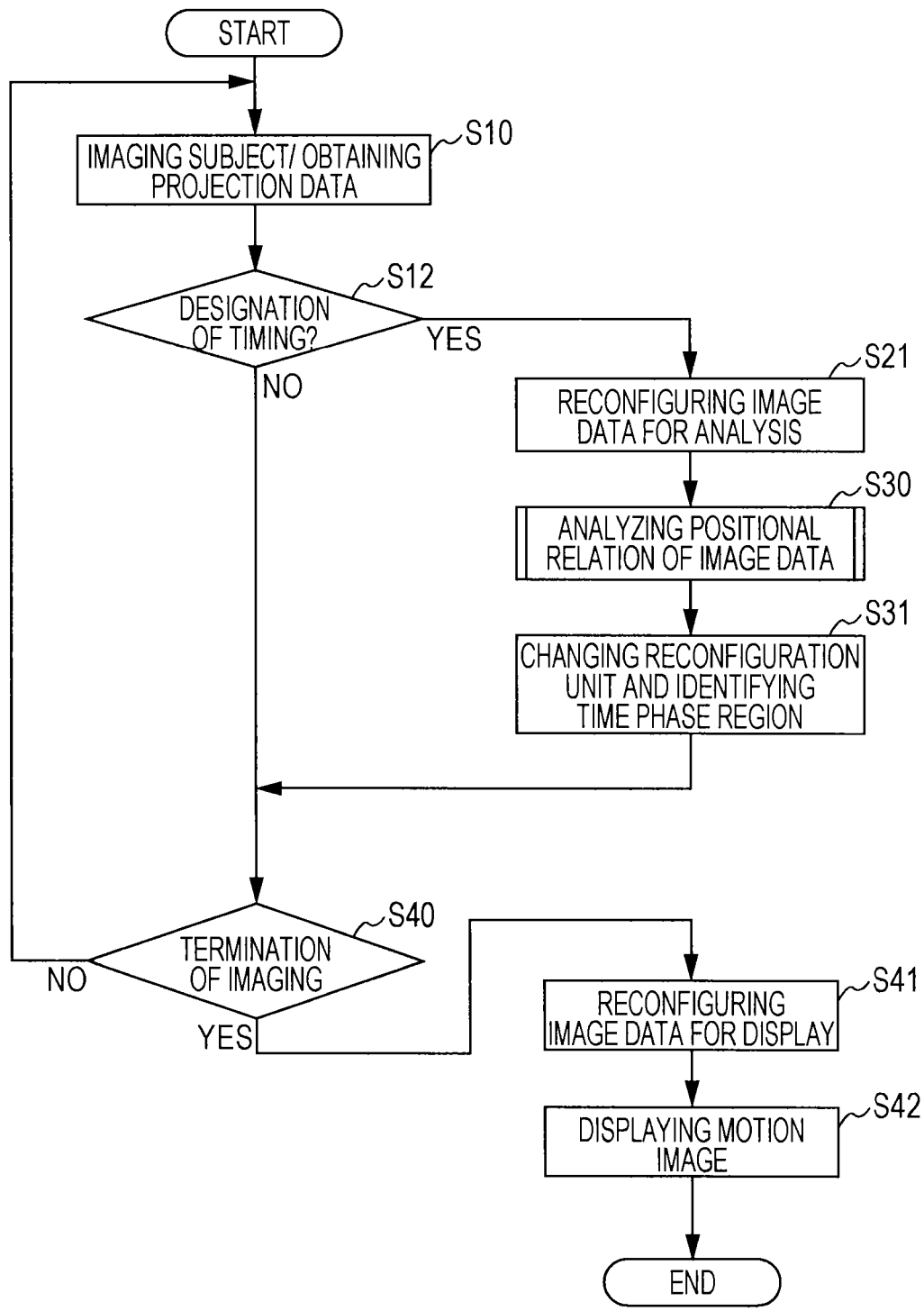
FIG. 4A is a flow chart showing a series of operations of the medical image processing apparatus pertaining to Embodiments 2 and 3.
Figure 6:
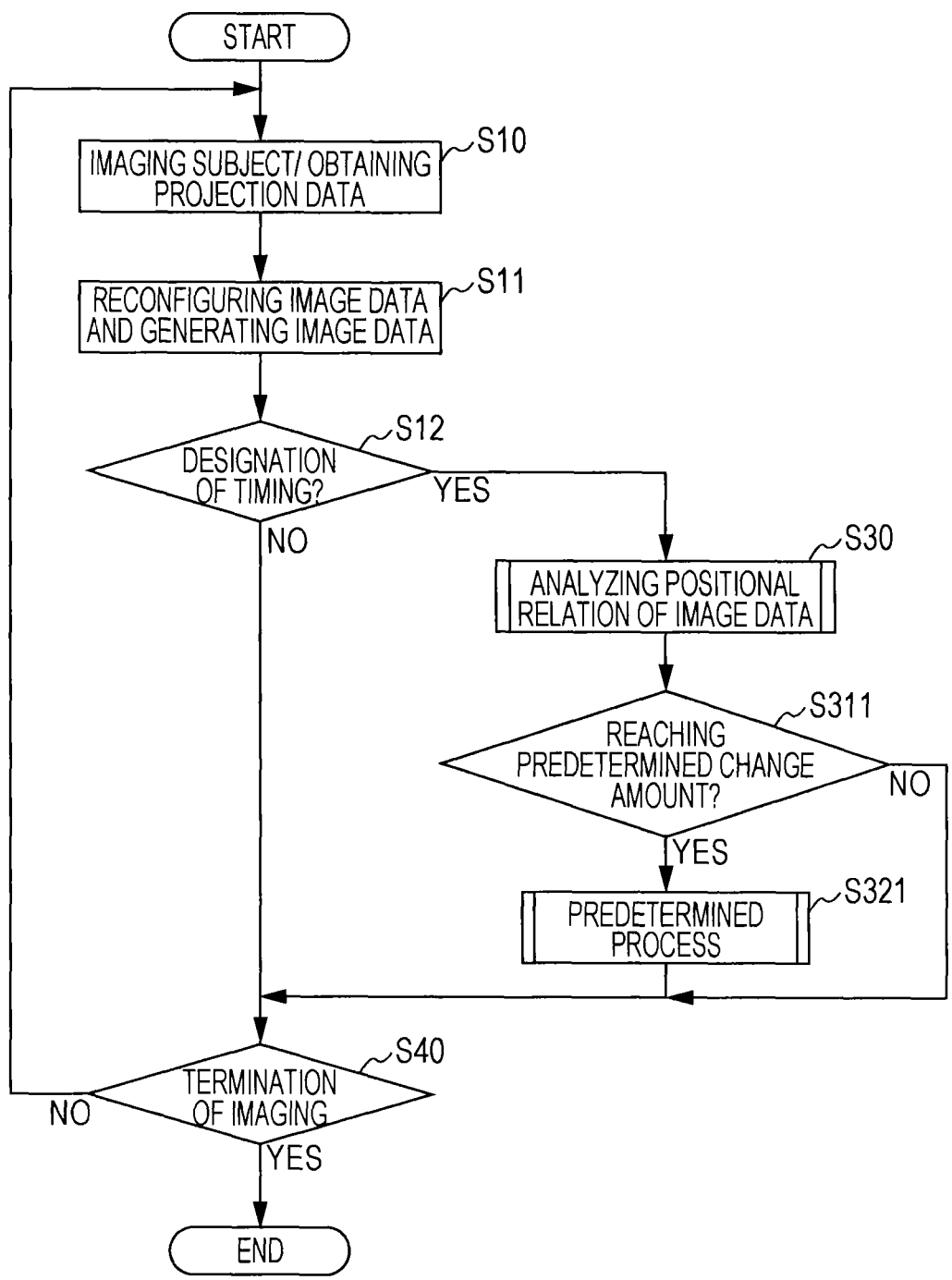
FIG. 6 is a flow chart showing a series of operations of the medical image processing apparatus pertaining to Embodiments 2 and 3.

Next, the series of operations of the medical image processing apparatus according to the present embodiment is explained with reference to FIG. 4A, FIG. 4B, and FIG. 6. FIG. 4A, FIG. 6 is flow charts showing a series of operations of the medical image processing apparatus according to the present embodiment. Moreover, FIG. 4B is a flow chart showing the operations related to analysis of the positional relation regarding the present embodiment. Furthermore, the flow chart illustrated in FIG. 4B corresponds to the process of Step S30 in FIGS. 4A and 6.

(Step S10)

When trigger signals are supplied from the X-ray controller 8, the high-voltage generator 7 drives the X-ray source 3. The high-voltage generator 7 applies a high voltage to the X-ray source 3 at the timing point of receiving the trigger signals. Thereby, X-rays are generated in the X-ray source 3, and the gantry/bed controller 9 synchronously controls the rotation of the rotating ring 2 of the gantry 1 and the slide of the sliding bed 6.

The detected elements configuring the X-ray detector 5 can measure the intensities of the X-rays generated by the X-ray source 3 in both the case in which the test object is present between the X-ray source 3 and the detected element, and the case in which it is not present. Accordingly, the respective detected elements measure at least one of the X-ray intensities, and output an analog signal corresponding to this intensity. The output signals from respective detected elements are read as distinguished for each column along the time sequence by the data accumulating unit 11 (that is, they are sequentially collected).

The data accumulating unit 11 comprises an integral amplifier and an A/D converter. Electric signals from respective detected elements included in the data accumulating unit 11 are time-divided through a common integral amplifier, and then converted into digital data by the A/D converter. The data accumulating unit 11 outputs signals converted into digital data from the detected element to the pretreating unit 12.

The pretreating unit 12 carries out processing such as correction by sensitivity on the digital data to be transmitted from the data accumulating unit 11 to turn this digital data into projected data. The pretreating unit 12 causes the projected data storage 13 to store this projected data as related to a column that is the reading origin of the digital data that is the generation origin of this projected data (Step S11, FIG. 6, in the Case of Changing the Scanning Conditions and the Scan Stopping Process)

The reconstruction processing unit 14 sequentially reads the obtained projected data from the projected data storage 13 in parallel with the processing for obtaining the projected data by means of the X-ray photographing unit 500. The reconstruction processing unit 14 carries out reconstruction processing on this read projected data based on conditions predetermined for analysis in advance, thereby generating image data for analysis for each timing point based on these reconstruction conditions. The reconstruction processing unit 14 stores the image data for analysis successively generated for each of the timing points in the image data storage 10.

(Step S12)

Moreover, the timing point specifying unit 512 receives specifications regarding the desired timing point from among the series of timing points in which photographing by the X-ray photographing unit 500 was carried out, and supplements the information indicating the timing points to the projected data (Step S12, Y). Specifically, as an example, when a reaction of the test object (for example, uttering from the test object) is detected from the microphone detecting the voice of the test object, the timing point specifying unit 512 receives notifications showing this. When a notification is received from the microphone, the timing point specifying unit 512 supplements the notification flag showing the timing point that receives the notification to the projected data acquired using the X-ray photographing unit 500. Moreover, without limitation to microphones, when specific reactions are detected from the test object using apparatuses monitoring reactions of the test object, such as, for example, cameras, heart rate meters, etc., the timing point specifying unit may operate by receiving notifications showing these reactions. Moreover, the timing point specifying unit 512 may also receive the specifications of the timing point from the operator via the operation part 402. For example, during photographing by the X-ray photographing unit 500, the operator gives instructions to the timing point specifying unit 512 via the operation part 402 at the desired timing point. The timing point specifying unit 512 should receive instructions by the operator from the operation part 402, and supplement the notification flag showing the timing points that received the instructions to the projected data. Furthermore, the medical image processing apparatus according to the present embodiment continues the series of operations until it receives the specifications on the desired timing points (Step S12, N), as long as it is not instructed to stop photographing (Step S40, N). Hereinafter, separate explanations are given because the process of changing the frame rate illustrated in FIG. 4A and the process of changing the scanning conditions as well as the scan stopping process illustrated in FIG. 6 are all different.

(In the Case of Changing the Frame Rate)
(Step S21)

The reconstruction processing unit 14 carries out reconstruction processing on the read projected data based on the reconstruction conditions for analysis determined in advance, thereby generating the image data for each timing point based on the reconstruction conditions. Furthermore, in the present embodiment, the reconstruction conditions are configured such that the surface portion (that is, the skin) of the test object may be extracted from the projected data. Thereby, the image data is reconstructed so as to be capable of extracting the surface portion. Moreover, when reconstructing the image data with respect to the timing points including the timing point shown by the notification flag supplemented to the projected data, the reconstruction processing unit 14 supplements to the image data the identification information for differentiating with other image data (that is, the "notification flag"). The reconstruction processing unit 14 stores the image data generated for each of the timing points in the image data storage 10.

(Step S301)

Here, 4B is referred. The configuration extracting unit 21 first reads the first image data reconstructed for analysis for each timing point. The configuration extracting unit 21 outputs the respective first image data for each read timing point to the object extracting part 211, providing instructions to extract the object.

The object extracting part 211 receives the first image data for each timing point from the configuration extracting unit 21. The object extracting part 211 detects the surface portion of test objects based on the voxel data in this image data, and extracts the outline object M21 within the range shaped from the extracted surface portion. Moreover, when the notification flag is supplemented to the first image data, the object extracting part 211 associates the notification flag to the information indicating the outline object M21 extracted from the image data. The object extracting part 211 outputs information indicating the outline object M21 extracted for each of the first image data at each timing point to the position analyzing unit 212 as related to the information indicating the corresponding timing point.

(Step S302)

The position analyzing unit 212 receives the information indicating the outline object M21 from the object extracting part 211 for each timing point. The position analyzing unit 212 analyzes changes in the outline along a time sequence based on this information. An example of a specific method thereof will be described below.

First, the position analyzing unit 212 specifies an object in which the outline object M21 supplemented with the notification flag becomes the standard from among the outline objects M21 for each timing point. Hereinafter, the outline object that becomes the standard may be referred to as the "standard object."

Once the standard object has been specified, the position analyzing unit 212 compares the standard object with the outline object for each timing point, and calculates the amount of change between the objects for each timing point. Specifically, the position analyzing unit 212 compares the shape of the two objects, and calculates the difference therebetween (for example, the number of pixels of areas not overlapping between the two) as the amount of change. Moreover, as an example of another method, the position analyzing unit 212 may extract axes from the upper arm and the lower arm, respectively, and the amount of change may be obtained based on the positional relation (for example, angle and angle) of the axes.

(Step S31)

Once the amount of change has been calculated for each timing point, the position analyzing unit 212 determines whether or not the calculated amount of change is within the amount determined in advance (hereinafter, referred to as the "standard value"), and specifies the time width shaped from the timing points in which the amount of change is within the standard. Thereby, by means of comparing the shape of the standard object and the outline object, the position analyzing unit 212 analyzes the positional relation of each part configuring the test object and specifies the time width in which the positional relation of the parts satisfies the predetermined conditions. Furthermore, the time width corresponds to the time width T21 in Embodiment 1 (refer to FIG. 2D), while the others correspond to the time widths T11 and T12. Hereinafter, the position analyzing unit 212 will be described assuming that this time width T21 is specified. The position analyzing unit 212 notifies the reconstruction processing unit 14 of the specified time width T21.

(Step S40)

Furthermore, the X-ray photographing unit 500 and the medical image processing apparatus according to the present embodiment carry out the abovementioned series of processes as long as they are not instructed to stop photographing by the operator (Step S40, N). Once it is instructed by the operator to terminate photographing (Step S40, Y), it transits to the next process.

(Steps S41, S42)

Furthermore, the operations hereinafter are the same as Embodiment 1. That is, the reconstruction processing unit 14 carries out reconstruction processing by changing the reconstruction conditions of the notified time width T21 and other time widths T11 and T12, reconstructing the image data for display for each timing point based on the reconstruction conditions. The reconstruction processing unit 14 stores the series of reconstructed image data for display in the image data storage 10. The image processor 22 carries out image processing on this image data and generates medical images, storing these in the image storage 23 as related to the information indicating the corresponding timing point. The display control 30 reads the medical images from the image storage 23 and displays motion images on the display 401 by arranging them along a time series.

As mentioned above, the medical image processing apparatus according to the present embodiment analyzes the change in positional relation of at least two or more parts configuring the flexible sites such as joints, etc. from the change in the outline of the test object. Moreover, in the medical image processing apparatus, the timing point specifying unit 512 is used as the external apparatus 51 to receive specifications on the desired timing point from among the series of time widths in which photographing by the X-ray photographing unit 500 was carried out, determining the outline shape corresponding to the timing point as the standard. On this basis, the medical image processing apparatus specifies the time width in which the amount of change of the outline in other timing points with respect to the standard is included within the predetermined range, carries out reconstruction processing within the time width and the other time widths by changing the reconstruction conditions, and reconstructs the image data for display. Thereby, the medical image processing apparatus according to the present embodiment becomes capable of displaying the time width in which the positional relation of two or more parts are included within the predetermined range at a higher frame rate than other time widths.

(In the Case of Changing the Scanning Conditions and the Scan Stopping Process)

Moreover, when reconstructing the image data with respect to the timing points including the timing point shown by the notification flag supplemented to the projected data, the reconstruction processing unit 14 supplements to the image data the identification information for differentiating with other image data (hereinafter, referred to as a "notification flag").

Furthermore, the medical image processing apparatus according to the present embodiment continues the series of operations until it receives the specifications regarding the desired timing points (Step S12, N), as long as it is instructed to stop photographing (Step S40, N).

(Step S201)

Here, FIG. 4B is referred. The configuration extracting unit 21 successively reads the image data for analysis, which is successively generated by the reconstruction processing unit 14 at each timing point and stored in the image data storage 10, from the image data storage 10. At this time, operations by the reconstruction processing unit 14 and operations related to reading the image data for analysis to the configuration extracting unit 21 may be synchronized. The configuration extracting unit 21 successively outputs the respective first image data for each read timing point to the object extracting part 211, providing instructions to extract the object from the first image data. The operation of this configuration extracting unit 21 is the same as in Embodiment 1.

The object extracting part 211 successively receives the first image data for each timing point from the configuration extracting unit 21. The object extracting part 211 according to the present embodiment detects the surface portion of the test objects based on the voxel data in the first image data, and extracts the object within the region shaped by the detected surface portion. This object shows the outline of the test object. Moreover, when the notification flag is supplemented to the first image data, the object extracting part 211 associates the notification flag to the information indicating the outline object M21 extracted from the image data. The object extracting part 211 outputs information indicating the outline object M21 extracted for each of the first image data at each timing point to the position analyzing unit 212 as related to the information indicating the corresponding timing point.

(Step S202)

The position analyzing unit 212 successively receives information indicating the outline object extracted from the object extracting part 211 for each timing point. The position analyzing unit 212 analyzes the change in the outline between each of the timing points based on the information. The position analyzing unit 212 specifies the outline object supplemented with the notification flag from among the successively received outline objects, and with the timing points corresponding to the outline object as the standard, it specifies the timing point controlling the operations related to acquiring the projected data of the X-ray photographing unit 500. An example of a specific method thereof will be described below.

The position analyzing unit 212 confirms whether or not the notification flag is supplemented to each outline object successively received for each timing point, and detects the outline object supplemented with the notification flag. When the external object supplemented with the notification flag is detected, the position analyzing unit 212 specifies the standard object of the outline object. Furthermore, hereinafter, the outline object that becomes the standard may be referred to as the "standard object."

Once the standard object has been specified, the position analyzing unit 212 compares this standard object with the outline object for each timing point, and calculates the amount of change between the objects for each timing point. Specifically, the position analyzing unit 212 compares the shape of the two objects, and calculates the difference therebetween (for example, the number of pixels of areas not overlapping between the two) as the amount of change. Moreover, as an example of another method, the position analyzing unit 212 may extract axes from the upper arm and the lower arm, respectively, and the amount of change may be obtained based on the positional relation (for example, position and direction) of the axes.

(Step S311)

Here, FIG. 6 is referred. Once the amount of change has been calculated, the position analyzing unit 212 determines whether or not the calculated amount of change is within the amount determined in advance (hereinafter, referred to as the "standard value"). The standard value should be determined based on, for example, the flexible range requiring attention with the standard object as the base point from among the series of movements of the observation subject. Thereby, the position analyzing unit 212 detects other timing points changed by within the standard value from among the one timing point with the shape of the outline object M21 coinciding with the standard object. That is, other timing points are detected with one timing point as the standard.

(Step S321)

When the position analyzing unit 212 detects other timing points with one timing point as the standard (Step S311, Y), it instructs the scan control 501 to change the scanning conditions or stop the scan. The scan control 501 receives the instructions and carries out the instructed operation (that is, it changes the scanning conditions or stops the scan). Furthermore, during the time in which the other timing points are not detected (Step S311, N), the position analyzing unit 212 does not give instructions to the scan control 501 and transits to the next process.
(Step S40)

Furthermore, the X-ray CT system according to the present embodiment carries out the series of processes unless instructions to stop photographing are given by the operator (Step S40, N). When instructions to stop photographing are given by the operator (Step S40, Y), the X-ray CT system according to the present embodiment terminates the process related to acquiring the projected data together with terminating the analysis processing for controlling this.

As mentioned above, the medical image processing apparatus according to the present embodiment analyzes the change in the positional relation of at least two or more parts configuring the flexible sites such as joints, etc. from the change in the outline of the test object. Moreover, in the medical image processing apparatus, the timing point specifying unit 512 is used as the external apparatus 51 to receive specifications on the desired timing point from among the series of time widths in which photographing by the X-ray photographing unit 500 was carried out, determining the outline shape corresponding to the timing point as the standard. On this basis, the medical image processing apparatus detects the timing point at which the amount of change with respect to the standard became the standard value or more and controls the operation related to acquiring the projected data based on this timing point (that is, it changes the scanning conditions or stops scanning). Thereby, in the X-ray CT system according to the present embodiment, the X-ray CT system itself can automatically control the operation for acquiring projected data without the operator when the positional relationship of two or more sites satisfies specific conditions.

(Embodiment 3)

Next, the medical image processing apparatus according to Embodiment 3 is explained. In the medical image processing apparatus according to Embodiment 2, the outline of the test object, that is, the time width that changes the reconstruction conditions and the timing point controlling the process related to acquiring the projected data based on the change in shape of the outline object M21, were specified. The medical image processing apparatus according to the present embodiment specifies the time width that changes the reconstruction conditions and the timing point controlling the process related to acquiring the projected data based on the positional relation of the bone object are specified. The medical image processing apparatus according to the present embodiment is explained in the following focusing on the parts different from Embodiment 2. Hereinafter, separate explanations are provided because the processing thereof differs in the case of changing the frame rate, changing the scanning conditions, and stopping the scan.

(In the Case of Changing the Frame Rate)

The reconstruction processing unit 14 according to the present embodiment first carries out reconstruction processing with respect to the read projected data based on the reconstruction conditions for analysis determined in advance, and then generates image data for each timing point based on the reconstruction conditions. Furthermore, in the present embodiment, the reconstruction conditions are configured such that the bone in the test object may be extracted from the projected data. That is, this image data is reconstructed so as to be capable of extracting bones. Furthermore, the bones include cartilage. Moreover, when reconstructing the image data with respect to the timing points including the timing point shown by the notification flag supplemented to the projected data, the reconstruction processing unit 14 supplements to the image data the notification flag for differentiating from other image data. Moreover, the image data generated based on the reconstruction conditions at this time corresponds to the "first image data." The reconstruction processing unit 14 stores the image data generated for each of the timing points in the image data storage 10.

Furthermore, the processing related to reconstruction of the image data for display of the reconstruction processing unit 14 related to the present embodiment is the same as the operation of the reconstruction processing unit 14 according to Embodiment 2. That is, the reconstruction processing unit 14 receives notification of the time width T21 comprising the plurality of timing points from the position analyzing unit 212. The reconstruction processing unit 14 carries out reconstruction processing while changing the reconstruction conditions between the notified time width T21 and other time widths T11 and T12, reconstructing the image data for display, and stores these in the image data storage 10.

The configuration extracting unit 21 first reads the first image data reconstructed for analysis for each timing point. The configuration extracting unit 21 outputs the respective first image data for each read timing point to the object extracting part 211, providing instructions to extract the object. The operation of the configuration extracting unit 21 is the same as Embodiment 2.

(In the Case of Changing the Scanning Conditions and the Scan Stopping Process)

The X-ray CT system according to the present embodiment analyzes the reconstructed image data, thereby comprehending the position and angle of each part configuring an observation subject as well as the relative positional relation thereof (hereinafter, this is generally simply referred to as the "positional relation").

Therefore, the reconstruction processing unit 14 reconstructs the image data for analysis separately from the image data for display. Specifically, the reconstruction processing unit 14 successively reads the acquired projected data from the projected data storage 13 in parallel with the processing related to acquiring the projected data using the X-ray photographing unit 500. The reconstruction processing unit 14 carries out reconstruction processing on the read projected data based on the reconstruction conditions for analysis determined in advance, thereby generating the image data for analysis for each timing point based on the reconstruction conditions.

In the present embodiment, the reconstruction conditions for reconstructing the image data for analysis are configured such that the bones in the test object may be extracted from the projected data. That is, the image data is reconstructed so as to be capable of extracting bones. Moreover, the image data generated based on the reconstruction conditions at this time corresponds to the "first image data." The reconstruction processing unit 14 stores the image data generated for each of the timing points in the image data storage 10. In the present embodiment, the positional relations of bones along the time sequence are analyzed based on bones of each part of the test objects reconstructed in this manner, and the timing point controlling the operations related to acquiring the projected data is specified by whether or not the positional relation satisfies the predetermined conditions.

Furthermore, the processing related to reconstruction of the image data for display of the reconstruction processing unit 14 related to the present embodiment is the same as the operation of the reconstruction processing unit 14 related to Embodiment 1. That is, the reconstruction processing unit 14 reads the projected data from the projected data storage 13 and carries out reconstruction processing based on the reconstruction conditions for display determined in advance, thereby generating image data for display for each timing point based on the reconstruction conditions. Furthermore, hereinafter, the image data generated based on the reconstruction conditions for display may be referred to as the "second image data." The reconstruction processing unit 14 stores the image data for display generated for the each timing point in the image data storage 10.

Furthermore, the image data for displaying does not necessarily need to be operated in parallel with the processing related to acquiring the projected data. For example, the reconstruction processing unit 14 may reconstruct the image for display after a series of projected data has been acquired. The operations are the same as in Embodiment 1.

The configuration extracting unit 21 successively reads the image data for analysis, which is successively generated by the reconstruction processing unit 14 at each timing point and stored in the image data storage 10, from the image data storage 10. At this time, operations by the reconstruction processing unit 14 and operations related to reading the image data for analysis to the configuration extracting unit 21 may be synchronized. The configuration extracting unit 21 successively outputs the respective first image data for each read timing point to the object extracting part 211, providing instructions to extract the object from the first image data. The operation of the configuration extracting unit 21 is the same as Embodiment 2.

(Commonalities in the Case of Changing the Frame Rate, Changing the Scanning Conditions, and the Scan Stopping Process)

Figure 5A:
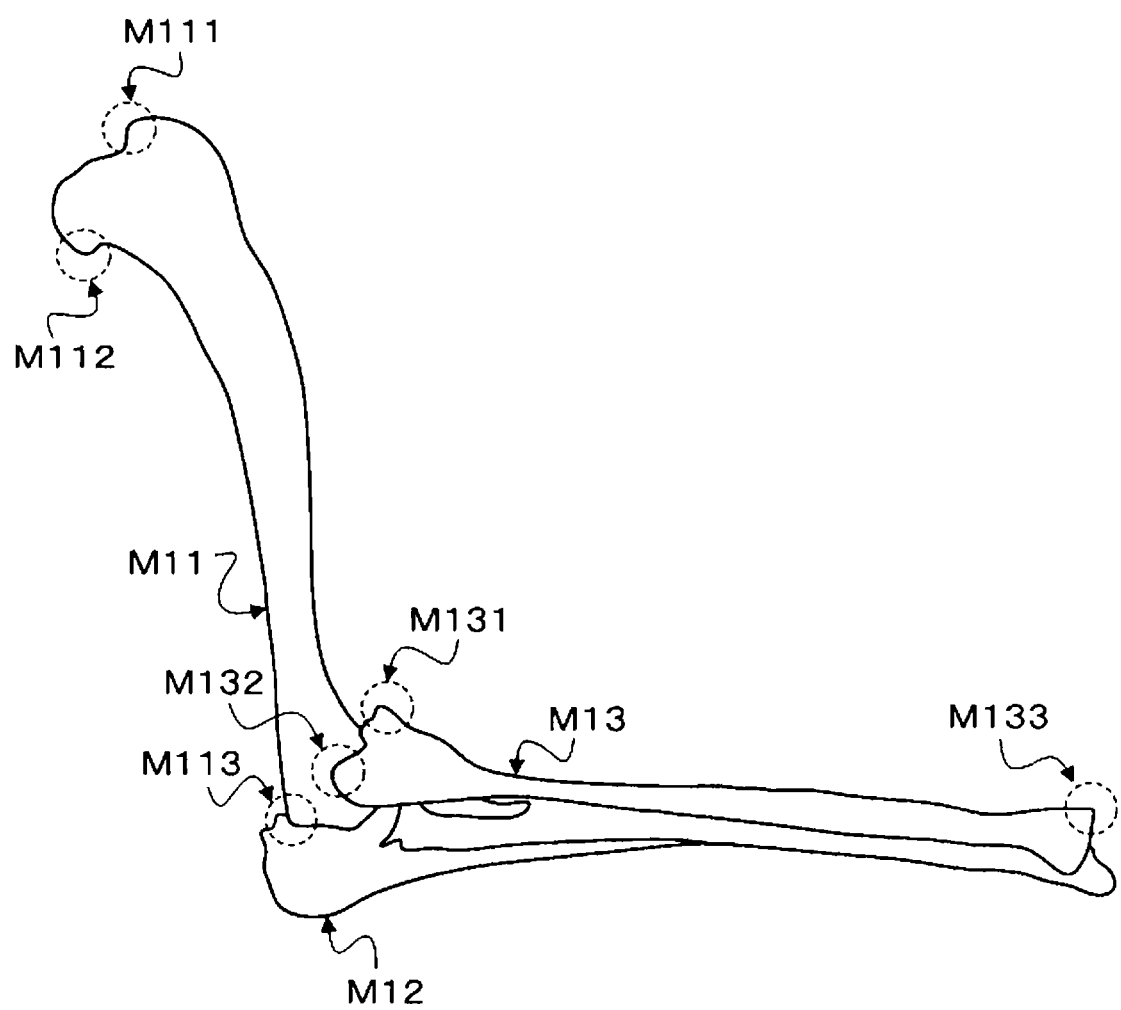
FIG. 5A is a diagram explaining the analysis of the positional relation in bones.

The object extracting part 211 receives the first image data for each timing point from the configuration extracting unit 21. The object extracting part 211 according to the present embodiment extracts the bone part as the object based on the voxel data in the first image data. Here, FIG. 5A is referred. FIG. 5A is a diagram for explaining analysis of the positional relation in bones, and shows an example when bone objects forming arm regions are extracted. As illustrated in FIG. 5A, the object extracting part 211 extracts bone objects M11, M12, and M13, forming arm regions, from the first image data. In this manner, the object extracting part 211 extracts the bone objects for all image data at each timing point. Moreover, when the notification flag is supplemented to the first image data, the object extracting part 211 associates the notification flag to the information indicating the bone object extracted from the image data. The object extracting part 211 outputs information indicating bone objects (for example, information indicating the form, the position, and the size of the object) extracted regarding the first image data of each timing point (in other words, extracted at each timing point) to the position analyzing unit 212, while relating them with the information indicating the corresponding timing point.

The position analyzing unit 212 receives information indicating the bone object at each timing point from the object extracting part 211. The position analyzing unit 212 analyzes the positional relation of the bone for each timing point based on the information. The position analyzing unit 212 specifies the information indicating the bone object supplemented with the notification flag from among the information indicating the successively received bone objects, and with the timing points corresponding to the outline object as the standard, it specifies the timing point controlling the operations related to acquiring the projected data of the X-ray photographing unit 500. An example of a specific method thereof will be described below.

The position analyzing unit 212 confirms whether or not the notification flag is supplemented to the respective information indicating the bone object successively received for each timing point, and detects information indicating the bone object supplemented with the notification flag. When the information indicating the bone objects supplemented with the notification flag is extracted, the position analyzing unit 212 specifies the positional relation of the bone objects and regards the positional relation of the specified bone object as the standard positional relation. The method for specifying the positional relation is explained in detail in the following.

The position analyzing unit 212 first specifies at least two or more objects (that is, the objects subject to observation) to be used for analyzing the positional relation from among bone objects M11, M12, and M13. Specifically, for example, the position analyzing unit 212 stores in advance the known bio-information of each part configuring a living body (for example, information indicating the positional relation of bones configuring the upper arm and lower arm), and specifies the object based on the bio-information. Moreover, as another method, the position analyzing unit 212 stores in advance the information indicating the shape of the object subject to observation, and specifies the object corresponding to this shape as the object subject to observation. Hereinafter, the position analyzing unit 212 is explained assuming that the objects M11 and M13 have been specified.

When the objects subject to analysis M11 and M13 are specified, the position analyzing unit 212 extracts at least three portions having characteristics in its shape (hereinafter, referred to as "shape characteristics") from the respective objects. For example, as illustrated in FIG. 5A, the position analyzing unit 212 extracts the shape characteristics M111, M112, and M113 from the object M11. Moreover, the position analyzing unit 212 extracts the shape characteristics M11, M12, and M13 from the object M13.

Figure 5B:
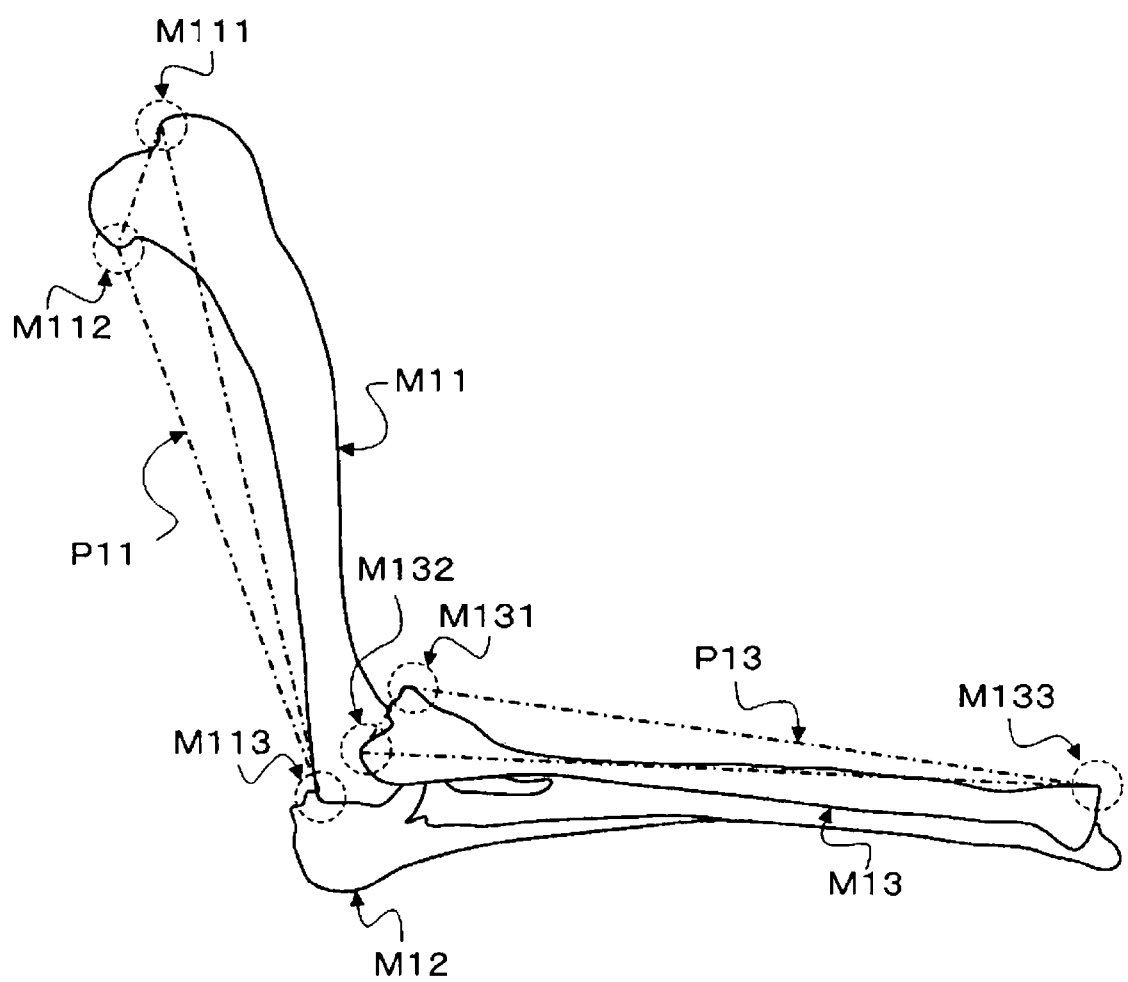
FIG. 5B is a diagram explaining the analysis of the positional relation in bones.

Next, the position analyzing unit 212 forms planes for comprehending the positions and directions of respective objects by simulation in portions (namely, points) indicating the extracted three points of shape features, relating the plane with the object that is the origin for extracting the shape features. Here, FIG. 5B is referred. FIG. 5B is a diagram explaining the analysis of the positional relationship of the bones, indicating a plane formed based on the shape features shaped by the respective objects M11 and M13. As illustrated in FIG. 5B, the position analyzing unit 212 shapes a plane P11 from the shape characteristics M11, M12, and M13, and associates these with the object M11. In the same manner, the position analyzing unit 212 shapes a plane P13 from the shape features M131, M132, and M133 and relates this to the object M13.

When joints are moved, the position and direction of each of a plurality of bones configuring the joint and the relative positional relationships thereof (hereinafter, they are simply referred to as the "positional relationship") are changed; however, the shape and size of each bone are not changed. In other words, the objects M11 and M13 extracted at each timing point are changed in the positional relationship at each timing point; however, the shape and size of each object are not changed. The same applies to the planes P11 and P13 extracted based on the shape feature of each object. According to the present embodiment, using this feature, the position analyzing unit 212 identifies the positional relationships of the objects M11 and M13 based on the position and direction of each of the planes P11 and P13 using the characteristics. Thus, by shaping a plane from each object, there is no need to carry out a complicated analysis on shapes in order to comprehend the position and direction of the object. Accordingly, the position analyzing unit 212 may reduce the processing load for identifying the positional relationships of the objects M11 and M13.

Figure 5C:
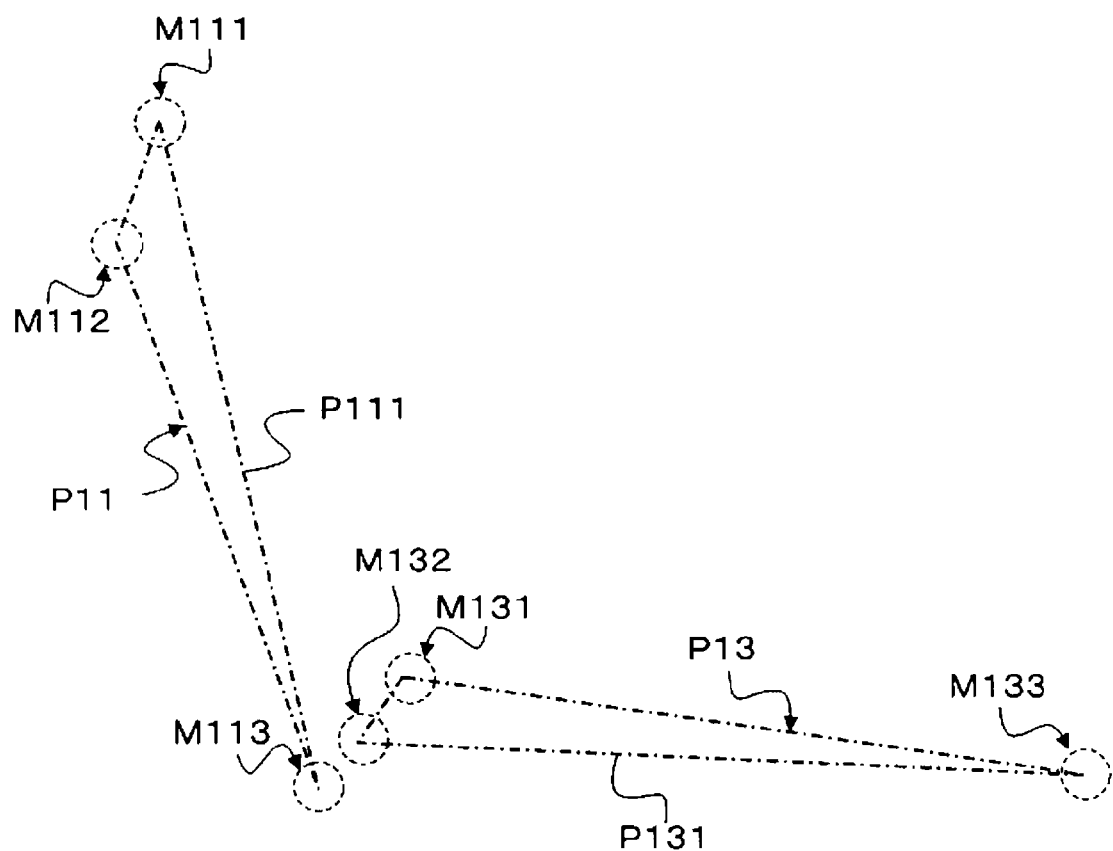
FIG. 5C is a diagram explaining the analysis of the positional relation in bones.

Here, FIG. 5C is referred. FIG. 5C is a diagram explaining the analysis of the positional relation in bones, indicating the positional relation of the objects M11 and M13 illustrated in FIG. 5A and FIG. 5B with planes P11 and P13. The position analyzing unit 212 specifies the relative positional relation of the objects M11 and M13 based on, for example, the angle configured by the planes P11 and P13. Moreover, the position analyzing unit 212 may specify the relative positional relation of the objects M11 and M13 based on the distance between the planes P11 and P13 instead of the angle. Furthermore, hereinafter, the position analyzing unit 212 is explained assuming that it specifies the positional relation of the objects M11 and M13 based on the planes P11 and P13.

Figure 5D:
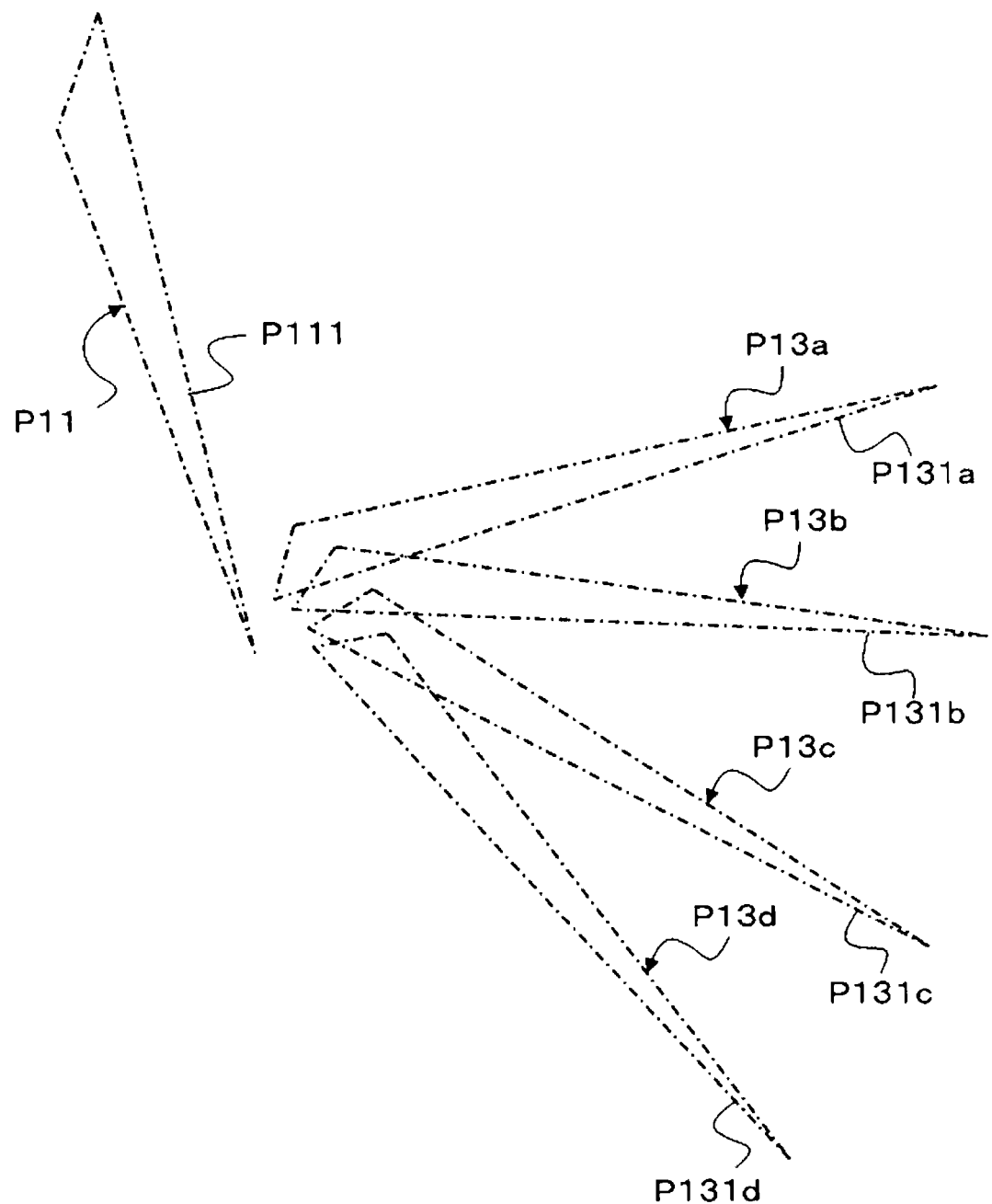
FIG. 5D is a diagram explaining the analysis of the positional relation in bones.

In this manner, the position analyzing unit 212 specifies the positional relation of the objects M11 and M13 based on the planes P11 and P13 extracted at each timing point. Here, FIG. 5D will be referred. FIG. 5D is a diagram explaining the analysis of the positional relation of the bones and illustrates an example of the positional relation of the planes P11 and P13 at multiple timing points. Furthermore, the example of FIG. 5D illustrates the change in position and direction of the plane P13 at each timing point assuming that the position and direction of the plane P11 (namely, the object M11) is the same, in order to make the explanation easier to comprehend. P13$a$ to P13$d$ in FIG. 5D illustrates the plane P13 corresponding to different timing points, respectively.

In addition, the position analyzing unit 212 is not limited to the above-described method based on the planes P11 and P13 if the positional relation of the objects M11 and M13 may be specified. For example, the relative positional relation of each object may be specified based on the outlines of each object M11 and M13. In this case, the position analyzing unit 212 specifies a 3-dimensional positional relation. Moreover, when specifying the 2-dimensional positional relation, a line connecting at least two shape characteristics may be extracted from the objects M11 and M13, and the positional relation may be specified based on the two extracted lines. For example, as illustrated in FIG. 5C and FIG. 5D, the line P111 is extracted based on the shape characteristics M111 and M113. Moreover, the line P131 is extracted based on the shape characteristics M132 and M133. The position analyzing unit 212 may specify the 2-dimensional positional relation of the objects M11 and M13 from the lines P111 and P113 extracted in this manner. In addition, the position and direction may be specified by carrying out positioning of the object itself based on pixel value information from the voxel construction of an object using Mutual Information. For example, based on the distribution of the pixel value information (information showing shading), it is possible to specify the position and direction of the object.

(In the Case of Changing the Frame Rate)

When the positional relation of the objects M11 and M13 are specified regarding a series of timing points, the position analyzing unit 212 specifies the positional relation corresponding to the information in which the notification flag is indicating the bone object as the positional relation to be the standard. Furthermore, hereinafter, the positional relation to be the standard may be referred to as a "standard positional relation."

Once the standard positional relation has been specified, the position analyzing unit 212 compares the standard positional relation with the positional relation of the objects M11 and M13, and calculates the amount of change in the positional relation for each timing point. For example, when the positional relation of the objects M11 and M13 is specified based on the angle configured by the planes P11 and P13, the difference in angle with the standard positional relation should be calculated as the amount of change.

Once the amount of change has been calculated for each timing point, the position analyzing unit 212 determines whether or not the calculated amount of change is within the amount determined in advance (hereinafter, referred to as a "standard value"), and specifies the time width shaped from the timing points in which the amount of change is within the standard. The standard value should be determined based on the flexible range requiring attention with the standard object as the base point from among the series of movements of the observation subject. Thereby, by means of comparing the shape of the standard object and the outline object, the position analyzing unit 212 analyzes the positional relation of each part configuring the test object and specifies the time width in which the positional relation of the parts satisfies the predetermined conditions. For example, FIG. 5E is a diagram explaining the time width specified by the position analyzing unit 212 regarding the present embodiment.

Figure 5E:
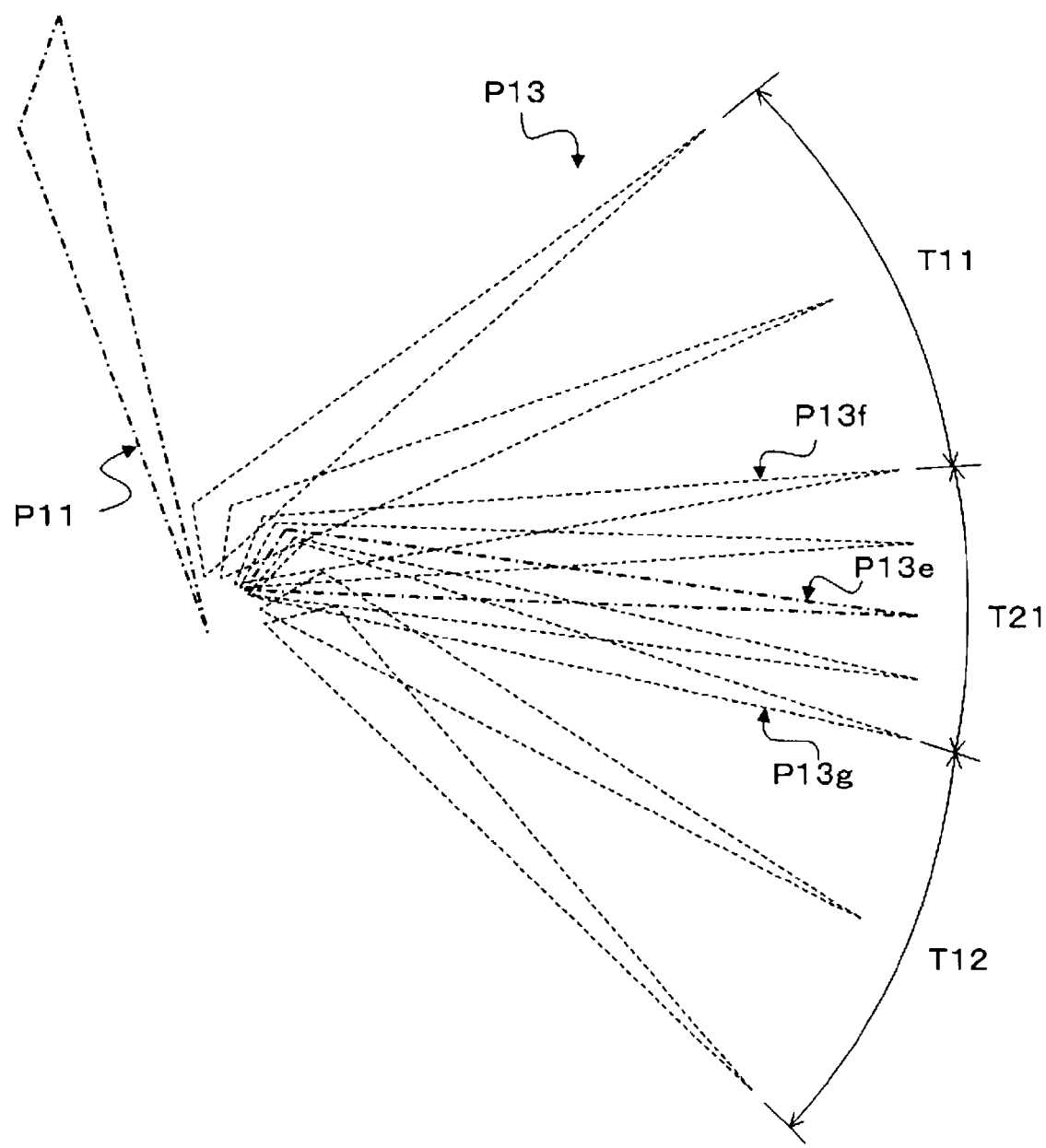
FIG. 5E is a diagram explaining the analysis of the positional relation in bones.

The planes P13$e$, P13$f$, and P13$g$ in FIG. 5E respectively show the position of the plane P13 corresponding to the object M13 when the positional relation of the objects M11 and M13 is included in the predetermined range. That is, this indicates that in the time width T21 shaped from the timing point corresponding to the plane P13$f$ to the timing point corresponding to the plane P13$g$, the positional relation of objects M11 and M13 is included in the predetermined range. The position analyzing unit 212 specifies the time width T21. Furthermore, the time width T21 in FIG. 5E corresponds to the time width T21 in FIG. 2D. Moreover, the time widths T11 and T12 correspond to the time widths T11 and T12 in FIG. 2D.

Figure 5F:
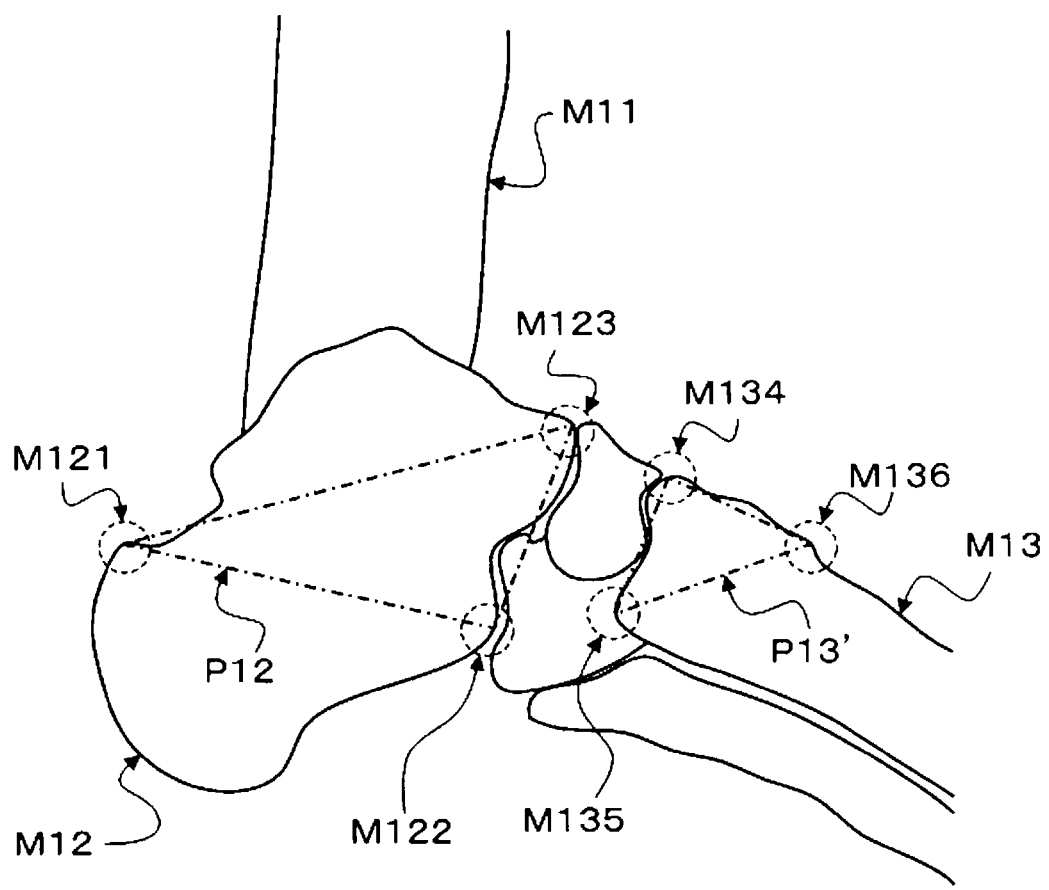
FIG. 5F is a diagram explaining the analysis of the positional relation in bones.

In addition, if the positional relation of the bones can be analyzed, it is not always necessary for whole images of respective bones such as the image of the upper arm and the lower arm to be photographed as illustrated in FIGS. 5A to 5C. For example, FIG. 5F shows the joint between the upper arm and the lower arm, and in this example, the objects M12 and M13 are identified as the subjects for analysis. In this case, the position analyzing unit 212 extracts the shape characteristics M121, M122, and M123 from the object M12. Moreover, the position analyzing unit 212 extracts the shape characteristics M134, M135, and M136 from the object M13. The position analyzing unit 212 extracts the plane P12 shaped by the shape characteristics M121, M122, and M123, and associates this with the object M12. In the same manner, the position analyzing unit 212 extracts the plane P13' shaped by the shape characteristics M134, M135, and M136, and associates this with the object M13. Hereinafter, the position analyzing unit 212 identifies the positional relation of the objects M12 and M13 based on the positional relation of the planes P12 and P13'. If the position and direction of each bone and the relative positional relation thereof may be identified in this manner based on the shape characteristics, the same process as the process mentioned above is possible even regarding cases in which the whole images of each part are not photographed, as in FIG. 5F.

The position analyzing unit 212 notifies the specified time width T21 to the reconstruction processing unit 14.

Moreover, the processes hereinafter are the same as in Embodiment 2. That is, the reconstruction processing unit 14 carries out reconstruction processing by changing the reconstruction conditions of the notified time width T21 and other time widths T11 and T12, reconstructing the image data for display for each timing point based on the reconstruction conditions. The reconstruction processing unit 14 stores the series of reconstructed image data for display in the image data storage 10. The image processor 22 carries out image processing on this image data and generates medical images, storing these in the image storage 23 as related to the information indicating the corresponding timing point. The display control 30 reads the medical images from the image storage 23 and displays motion images on the display 401 by arranging them along a time series.

Next, the series of operations of the medical image processing apparatus according to the present embodiment is explained, with reference to FIG. 4A and FIG. 4C. FIG. 4C is a flow chart showing the series of operations of the medical image processing apparatus according to the present embodiment. Moreover, 4C is a flow chart showing the operations related to the analysis of the positional relation in the present embodiment. Furthermore, the flow chart shown in FIG. 4C corresponds to the process of step S30 of FIG. 4A. Moreover, other than the processes related to Steps S21, S30, and S31 of FIG. 4A, it is the same as Embodiment 1. Accordingly, explanations are given focusing on the processes that are different from Embodiment 1, including steps S21, S30 (that is, S303 and S304), as well as S31.

(Step S21)

The reconstruction processing unit 14 according to the present embodiment first carries out reconstruction processing with respect to the read projected data based on the reconstruction conditions for analysis determined in advance, and then generates image data for each timing point based on the reconstruction conditions. Furthermore, in the present embodiment, the reconstruction conditions are configured such that the bone in the test object may be extracted from the projected data. That is, this image data is reconstructed so as to be capable of extracting bones. Moreover, when reconstructing the image data with respect to the timing points including the timing point shown by the notification flag supplemented to the projected data, the reconstruction processing unit 14 supplements to the image data the notification flag for differentiating from other image data. Moreover, the image data generated based on the reconstruction conditions at this time corresponds to the "first image data." The reconstruction processing unit 14 stores the image data generated for each of the timing points in the image data storage 10.

(Step S303)

The configuration extracting unit 21 first reads the first image data reconstructed for analysis for each timing point. The configuration extracting unit 21 outputs the respective first image data for each read timing point to the object extracting part 211, providing instructions to extract the object. The operation of the configuration extracting unit 21 is the same as Embodiment 2.

The object extracting part 211 receives the first image data for each timing point from the configuration extracting unit 21. The object extracting part 211 according to the present embodiment extracts the bone part as the object based on the voxel data in the first image data. Here, FIG. 5A is referred. FIG. 5A is a diagram explaining the analysis of the positional relation in bones, and shows an example when bone objects forming arm regions are extracted. As illustrated in FIG. 5A, the object extracting part 211 extracts bone objects M11, M12, and M13, forming arm regions, from the first image data. In this manner, the object extracting part 211 extracts the bone objects for all image data at each timing point. Moreover, when the notification flag is supplemented to the first image data, the object extracting part 211 associates the notification flag with the information indicating the bone object extracted from the image data. The object extracting part 211 outputs information indicating bone objects (for example, information indicating the form, the position, and the size of the object) extracted regarding the first image data of each timing point (in other words, extracted at each timing point) to the position analyzing unit 212, while relating them with the information indicating the corresponding timing point.

(Step S304)

The position analyzing unit 212 receives information indicating the bone object at each timing point from the object extracting part 211. The position analyzing unit 212 analyzes the positional relation of the bone for each timing point based on the information. An example of a specific method thereof will be described below.

The position analyzing unit 212 first specifies at least two or more objects (that is, the objects subject to observation) to be used for analyzing the positional relation from among bone objects M11, M12, and M13. Specifically, for example, the position analyzing unit 212 stores in advance the known bio-information of each part configuring a living body (for example, information indicating the positional relation of bones configuring the upper arm and lower arm), and specifies the object based on the bio-information. Moreover, as another method, the position analyzing unit 212 stores in advance the information indicating the shape of the object subject to observation, and specifies the object corresponding to this shape as the object subject to observation. Hereinafter, the position analyzing unit 212 is explained assuming that the objects M11 and M13 have been specified.

When the objects subject to analysis M11 and M13 are specified, the position analyzing unit 212 extracts at least three portions having characteristics in its shape (hereinafter, referred to as "shape characteristics") from the respective objects. For example, as illustrated in FIG. 5A, the position analyzing unit 212 extracts the shape characteristics M111, M112, and M113 from the object M11. Moreover, the position analyzing unit 212 extracts the shape characteristics M131, M132, and M133 from the object M13.

Next, the position analyzing unit 212 forms planes for comprehending the positions and angles of respective objects by simulation in portions (namely, points) indicating the extracted three shape characteristics, relating the plane with the object that is the base point for extracting the shape characteristics. Here, FIG. 5B will be referred. FIG. 5B is a view explaining the analysis of the positional relation of the bones, and FIG. 3B illustrates the planes formed based on the shape characteristics formed by the objects M11 and M13, respectively. As illustrated in FIG. 5B, the position analyzing unit 212 forms a plane P11 according to shape characteristics M111, M112, and M113, relating this plane with the object M11. In the same manner, the position analyzing unit 212 shapes a plane P13 from the shape features M131, M132, and M133 and relates this to the object M13.

Here, FIG. 5C is referred. FIG. 5C is a diagram explaining the analysis of the positional relation in bones, indicating the positional relation of the objects M11 and M13 illustrated in FIG. 5A and FIG. 5B with planes P11 and P13. The position analyzing unit 212 specifies the relative positional relation of the objects M11 and M13 based on, for example, the angle configured by the planes P11 and P13. Moreover, the position analyzing unit 212 may specify the relative positional relation of the objects M11 and M13 based on the distance between the planes P11 and P13 by replacing the angle. Furthermore, hereinafter, the position analyzing unit 212 is explained assuming that it specifies the positional relation of the objects M11 and M13 based on the planes P11 and P13.

In this manner, the position analyzing unit 212 specifies the positional relation of the objects M11 and M13 based on the planes P11 and P13 extracted at each timing point. Here, FIG. 5D will be referred. FIG. 5D is a diagram explaining the analysis of the positional relation of the bones and illustrates an example of the positional relation of the planes P11 and P13 at multiple timing points. Furthermore, the example of FIG. 5D illustrates the change in the position and direction of the plane P13 at each timing point assuming that the position and direction of the plane P11 (namely, the object M11) is the same, in order to make the explanation easier to comprehend. P13a to P13d in FIG. 5D illustrate the plane P13 corresponding to different timing points, respectively.

(Step S31)

When the positional relation of the objects M11 and M13 are specified regarding a series of timing points, the position analyzing unit 212 specifies the positional relation corresponding to the information in which the notification flag indicates the bone object as the positional relation to be the standard. Furthermore, hereinafter, the positional relation to be the standard may be referred to as the "standard positional relation."

Once the standard positional relation has been specified, the position analyzing unit 212 compares the standard positional relation with the positional relation of the objects M11 and M13, and calculates the amount of change in the positional relation for each timing point. For example, when the positional relation of the objects M11 and M13 is specified based on the angle configured by the planes P11 and P13, the difference in the angle with the standard positional relation should be calculated as the amount of change.

Once the amount of change has been calculated for each timing point, the position analyzing unit 212 determines whether or not the calculated amount of change is within the amount determined in advance (hereinafter, referred to as the "standard value"), and specifies the time width shaped from the timing points in which the amount of change is within the standard. The standard value should be determined based on the flexible range requiring attention with the standard object as the base point from among the series of movements of the observation subject. Thereby, by means of comparing the shape of the standard object and the outline object, the position analyzing unit 212 analyzes the positional relation of each part configuring the test object and specifies the time width in which the positional relation of the parts satisfies the predetermined conditions. For example, FIG. 5E is a diagram explaining the time width specified by the position analyzing unit 212 regarding the present embodiment.

The planes P13e, P13f, and P13g in FIG. 5E respectively show the position of the plane P13 corresponding to the object M13 when the positional relation of the objects M11 and M13 is included in the predetermined range. That is, this indicates that in the time width T21 shaped from the timing point corresponding to the plane P13f to the timing point corresponding to the plane P13g, the positional relation of objects M11 and M13 is included in the predetermined range. The position analyzing unit 212 specifies the time width T21. Furthermore, the time width T21 in FIG. 5E corresponds to the time width T21 in FIG. 2D. Moreover, the time widths T11 and T12 correspond to the time widths T11 and T12 in FIG. 2D.

The position analyzing unit 212 notifies the specified time width T21 to the reconstruction processing unit 14.

Moreover, the processes hereinafter are the same as in Embodiment 2. That is, the reconstruction processing unit 14 carries out reconstruction processing by changing the reconstruction conditions of the notified time width T21 and other time widths T11 and T12, reconstructing the image data for display for each timing point based on the reconstruction conditions. The reconstruction processing unit 14 stores the series of reconstructed image data for display in the image data storage 10. The image processor 22 carries out image processing on this image data and generates medical images, storing these in the image storage 23 as related to the information indicating the corresponding timing point. The display control 30 reads the medical images from the image storage 23 and displays motion images on the display 401 by arranging them along a time series.

As described above, the medical image processing apparatus according to the present embodiment analyzes changes in the positional relationship of at least two sites that configure flexible sites such as joints, etc. by means of the bone objects corresponding to these sites. Moreover, in the same manner as Embodiment 2, in the medical image processing apparatus according to the present embodiment, the timing point specifying unit 512 is used as the external apparatus 51 to receive specifications at the desired timing point from among the series of timing points at which photographing by the X-ray photographing unit 500 was carried out, determining the positional relation of the bone corresponding to the timing point as the standard. On this basis, the medical image processing apparatus specifies the time width in which the amount of change of the positional relation of bones in other timing points with respect to the standard is included within the predetermined range, carries out reconstruction processing within the time width and the other time widths by changing the reconstruction conditions, and reconstructs the image data for display. Thereby, in the same manner as Embodiment 2, the medical image processing apparatus according to the present embodiment may display medical images at a frame rate higher than other time widths with respect to a time width having a positional relationship of two or more sites included in a specific range.

(In the Case of Changing the Scanning Conditions and the Scan Stopping Process)

In this manner, the position analyzing unit 212 detects the information of the bone object supplemented with the notification flag and then specifies the positional relation of the bone at this time as the standard positional relation. Once the standard positional relation is specified, the position analyzing unit 212 specifies the positional relation of the bone object, which is the subject for observation, regarding the information indicating each bone object successively received at each time phase from the timing point onwards, that is, after the timing points. Here, FIG. 5D is referred. FIG. 5D is a diagram explaining the analysis of the positional relation of the bones and illustrates an example of the positional relation of the planes P11 and P13 at multiple timing points. Furthermore, the example of FIG. 5D illustrates the change in position and direction of the plane P13 at each timing point assuming that the position and direction of the plane P11 (namely, the object M11) is the same, in order to make the explanation easier to comprehend. P13a to P13d in FIG. 5D illustrates the plane P13 corresponding to different timing points, respectively.

When the positional relation of each bone is specified, the position analyzing unit 212 compares the positional relation of the objects M11 and M13 specified at each timing point with the standard positional relation, and successively calculates the amount of change in the positional relation for each timing point. For example, when the positional relation of the objects M11 and M13 is specified based on the angle configured by the planes P11 and P13, the difference in angle with the standard positional relation should be calculated as the amount of change.

Once the amount of change has been calculated, the position analyzing unit 212 determines whether or not the calculated amount of change is within the amount determined in advance (hereinafter, referred to as the "standard value"). The standard value should be determined based on, for example, the flexible range requiring attention with the timing point corresponding to the standard positional relation as the base point from among the series of movements of the observation subject. Thereby, the position analyzing unit 212 detects other timing points in which the positional relation is changed by within the standard value from among the one timing point with the positional relation of the objects M11 and M13 coinciding with the standard positional relation. That is, other timing points are detected with one timing point as the standard.

When the position analyzing unit 212 detects other timing points with one timing point as the standard, it instructs the scan control 501 to change the scanning conditions or stop the scan. The scan control 501 receives the instructions and carries out the instructed operation (that is, it changes the scanning conditions or stops the scan). Furthermore, which among changing the scanning conditions and stopping the scan to be instructed should be associated in advance with the information indicating the detected timing points (in other words, the positional relation corresponding to the timing point thereof).

Furthermore, the operations hereinafter are the same as Embodiment 2. That is, when the second image data reconstructed for display is stored in the image data storage 10, the configuration extracting unit 21 reads this and transfers it to the image processor 22. Furthermore, the first image data generated for analysis may be operated such that it may be additionally used for display. In this case, the position analyzing unit 212 should transfer the image data that has already been read for analysis to the image processor 22. The image processor 22 carries out image processing on this image data and generates medical images, storing these in the image storage 23 as related to the information indicating the corresponding timing point. The display control 30 reads the medical images from the image storage 23 and displays motion images on the display 401 by arranging them along a time series.

Next, the series of operations of the X-ray CT system according to the present embodiment is explained, with reference to FIG. 4A and FIG. 4C. FIG. 4C is a flow chart showing the series of operations of the medical image processing apparatus according to the present embodiment. Furthermore, the flow chart shown in FIG. 4C corresponds to the process of step S20 of FIG. 4A. Moreover, other than the processes related to Steps S11, S20, S31, and S32 of FIG. 4A, it is the same as Embodiment 1. Accordingly, explanations are provided focusing on processes that are different from Embodiment 1, including steps S11, S20 (that is, S203 and S204), S31, and S32.

(Step S11)

The X-ray CT system according to the present embodiment analyzes the reconstructed image data, thereby comprehending the position and angle of each part configuring an observation subject as well as the relative positional relation thereof (hereinafter, this is generally simply referred to as the "positional relation"). Therefore, the reconstruction processing unit 14 reconstructs the image data for analysis separately from the image data for display. Specifically, the reconstruction processing unit 14 successively reads the acquired projected data from the projected data storage 13 in parallel with the processing related to acquiring the projected data using the X-ray photographing unit 500. The reconstruction processing unit 14 carries out reconstruction processing on the read projected data based on the reconstruction conditions for analysis determined in advance, thereby generating the image data for analysis for each timing point based on the reconstruction conditions.

In the present embodiment, the reconstruction conditions for reconstructing the image data for analysis are configured such that the bones in the test object may be extracted from the projected data. That is, the image data is reconstructed so as to be capable of extracting bones. Moreover, the image data generated based on the reconstruction conditions at this time corresponds to the "first image data." The reconstruction processing unit 14 stores the image data generated for each of the timing points in the image data storage 10.

(Step S12)

Moreover, the timing point specifying unit 512 receives specifications regarding the desired timing point from among the series of timing points in which photographing by the X-ray photographing unit 500 was carried out, and supplements the information indicating the timing points to the projected data (Step S12, Y). Specifically, as an example, when a reaction of the test object (for example, uttering from the test object) is detected from the microphone detecting the voice of the test object, the timing point specifying unit 512 receives notifications showing this. When the notification is received from the microphone, the timing point specifying unit 512 supplements the notification flag showing the timing point that receives the notification to the projected data acquired by the X-ray photographing unit 500. Moreover, without limitation to microphones, when specific reactions are detected from the test object using apparatuses monitoring reactions of the test object, such as, for example, cameras, heart rate meters, etc., the timing point specifying unit may operate by receiving notifications showing these reactions. Moreover, the timing point specifying unit 512 may also receive the specifications of the timing point from the operator via the operation part 402. For example, during photographing by the X-ray photographing unit 500, the operator gives instructions to the timing point specifying unit 512 via the operation part 402 at the desired timing point. The timing point specifying unit 512 should receive instructions by the operator from the operation part 402, and supplement the notification flag showing the timing points that received the instructions to the projected data.

Moreover, when reconstructing the image data with respect to the timing points including the timing point shown by the notification flag supplemented to the projected data, the reconstruction processing unit 14 supplements to the image data the identification information for differentiating from other image data (hereinafter, referred to as a "notification flag").

Furthermore, the medical image processing apparatus according to the present embodiment continues the series of operations until it receives the specifications regarding the desired timing points (Step S12, N), as long as it is instructed to stop photographing (Step S13, N).

(Step S203)

Here, FIG. 4C is referred. The configuration extracting unit 21 successively reads the image data for analysis, which is successively generated by the reconstruction processing unit 14 at each timing point and stored in the image data storage 10, from the image data storage 10. At this time, operations by the reconstruction processing unit 14 and operations related to reading the image data for analysis to the configuration extracting unit 21 may be synchronized. The configuration extracting unit 21 successively outputs the respective first image data for each read timing point to the object extracting part 211, providing instructions to extract the object from the first image data. The operation of the configuration extracting unit 21 is the same as Embodiment 2.

The object extracting part 211 successively receives the first image data for each timing point from the configuration extracting unit 21. In this manner, the object extracting part 211 according to the present embodiment extracts the bone part as the object based on the voxel data in the first image data. Here, FIG. 5A is referred. FIG. 5A is a diagram explaining the analysis of the positional relation in bones, and shows an example when bone objects forming arm regions are extracted. As illustrated in FIG. 5A, the object extracting part 211 extracts bone objects M11, M12, and M13, forming arm regions, from the first image data. In this manner, the object extracting part 211 extracts the bone objects for all image data at each timing point. Moreover, when the notification flag is supplemented to the first image data, the object extracting part 211 associates the notification flag to the information indicating the bone object extracted from the image data. The object extracting part 211 outputs information indicating bone objects (for example, information indicating the form, the position, and the size of the object) extracted regarding the first image data of each timing point (in other words, extracted at each timing point) to the position analyzing unit 212, while relating them with the information indicating the corresponding timing point.

(Step S204)

The position analyzing unit 212 receives information indicating the bone object at each timing point from the object extracting part 211. The position analyzing unit 212 analyzes the change in the positional relation of the bone along the time series based on the information. The position analyzing unit 212 specifies the outline object supplemented with the notification flag from among the information indicating the successively received outline objects, and with the timing points corresponding to the outline object as the standard, it specifies the timing point controlling the operations related to acquiring the projected data of the X-ray photographing unit 500.

The position analyzing unit 212 confirms whether or not the notification flag is supplemented to the respective information indicating the bone object successively received for each timing point, and detects information indicating the bone object supplemented with the notification flag. When the information indicating the bone objects supplemented with the notification flag is extracted, the position analyzing unit 212 specifies the positional relation of the bone objects and regards the positional relation of the specified bone object as the standard positional relation. The method for specifying the positional relation is explained in detail in the following.

The position analyzing unit 212 first specifies at least two or more objects (that is, the objects subject to observation) to be used for analyzing the positional relation from among bone objects M11, M12, and M13. Specifically, for example, the position analyzing unit 212 stores in advance the known bio-information of each part configuring a living body (for example, information indicating the positional relation of bones configuring the upper arm and lower arm), and specifies the object based on the bio-information. Moreover, as another method, the position analyzing unit 212 stores in advance the information indicating the shape of the object subject to observation, and specifies the object corresponding to this shape as the object subject to observation. Hereinafter, the position analyzing unit 212 is explained assuming that the objects M11 and M13 have been specified.

When the objects subject to analysis M11 and M13 are specified, the position analyzing unit 212 extracts at least three portions having characteristics in its shape (hereinafter, referred to as "shape characteristics") from the respective objects. For example, as illustrated in FIG. 5A, the position analyzing unit 212 extracts the shape characteristics M111, M112, and M113 from the object M11. Moreover, the position analyzing unit 212 extracts the shape characteristics M11, M12, and M13 from the object M13.

Next, the position analyzing unit 212 forms planes for comprehending the positions and directions of respective objects by simulation in portions (namely, points) indicating the extracted three points of shape features, relating the plane with the object that is the origin for extracting the shape features. Here, FIG. 5B is referred. FIG. 5B is a diagram explaining the analysis of the positional relationship of the bones, indicating a plane formed based on the shape features shaped by the respective objects M11 and M13. As illustrated in FIG. 5B the position analyzing unit 212 shapes a plane P11 from the shape characteristics M111, M112, and M113, and associates these with the object M11. In the same manner, the position analyzing unit 212 shapes a plane P13 from the shape features M131, M132, and M133 and relates this to the object M13.

When joints are moved, the position and direction of each of a plurality of bones configuring the joint and the relative positional relationships thereof (hereinafter, they are simply referred to as the "positional relationship") are changed; however, the shape and size of each bone are not changed. In other words, the objects M11 and M13 extracted at each timing point are changed in the positional relationship at each timing point; however, the shape and size of each object are not changed. The same applies to the planes P11 and P13 extracted based on the shape feature of each object. According to the present embodiment, using this feature, the position analyzing unit 212 identifies the positional relationships of the objects M11 and M13 based on the position and direction of each of the planes P11 and P13 using the characteristics. Thus, by shaping a plane from each object, there is no need to carry out a complicated analysis on shapes in order to comprehend the position and direction of the object. Accordingly, the position analyzing unit 212 may reduce the processing load for identifying the positional relationships of the objects M11 and M13.

Here, FIG. 5C is referred. FIG. 5C is a diagram explaining the analysis of the positional relation in bones, indicating the positional relation of the objects M11 and M13 illustrated in FIG. 5A and FIG. 5B with planes P11 and P13. The position analyzing unit 212 specifies the relative positional relation of the objects M11 and M13 based on, for example, the angle configured by the planes P11 and P13. Moreover, the position analyzing unit 212 may specify the relative positional relation of the objects M11 and M13 based on the distance between the planes P11 and P13 by replacing the angle. Furthermore, hereinafter, the position analyzing unit 212 is explained assuming that it specifies the positional relation of the objects M11 and M13 based on the planes P11 and P13.

In this manner, the position analyzing unit 212 detects the information of the bone object supplemented with the notification flag and then specifies the positional relation of the bone at this time as the standard positional relation. Once the standard positional relation is specified, the position analyzing unit 212 specifies the positional relation of the bone object, which is the subject for observation, regarding the information indicating each bone object successively received at each time phase from the timing point onwards, that is, after the timing points. Here, FIG. 5D will be referred. FIG. 5D is a diagram explaining the analysis of the positional relation of the bones and illustrates an example of the positional relation of the planes P11 and P13 at multiple timing points. Furthermore, the example of FIG. 5D illustrates the change in position and direction of the plane P13 at each timing point assuming that the position and direction of the plane P11 (namely, the object M11) is the same, in order to make the explanation easier to comprehend. P13a to P13d in FIG. 5D illustrates the plane P13 corresponding to different timing points, respectively.

When the positional relation of each bone is specified, the position analyzing unit 212 compares the positional relation of the objects M11 and M13 specified at each timing point with the standard positional relation, and successively calculates the amount of change in the positional relation for each timing point. For example, when the positional relation of the objects M11 and M13 is specified based on the angle configured by the planes P11 and P13, the difference in angle with the standard positional relation should be calculated as the amount of change.
(Step S31)

Here, FIG. 4A is referred. Once the amount of change has been calculated, the position analyzing unit 212 determines whether or not the calculated amount of change is within the amount determined in advance (hereinafter, referred to as the "standard value"). The standard value should be determined based on the flexible range requiring attention with the timing point corresponding to the standard positional relation as the base point from among the series of movements of the observation subject. Thereby, the position analyzing unit 212 detects other timing points in which the positional relation is changed by within the standard value from among the one timing point with the positional relation of the objects M11 and M13 coinciding with the standard positional relation. That is, other timing points are detected with one timing point as the standard.
(Step S32)

When the position analyzing unit 212 detects other timing points with one timing point as the standard (Step S31, Y), it instructs the scan control 501 to change the scanning conditions or stop the scan. The scan control 501 receives the instructions and carries out the instructed operation (that is, it changes the scanning conditions or stops the scan). Furthermore, during the time in which the other timing points are not detected (Step S31, N), the position analyzing unit 212 does not give instructions to the scan control 501 and transits to the next process.
(Step S13)

Furthermore, the X-ray CT system according to the present embodiment carries out the series of processes unless instructions to stop photographing are given by the operator (Step S13, N). When instructions to stop photographing are given by the operator (Step S13, Y), the X-ray CT system according to the present embodiment terminates the process related to acquiring the projected data together with terminating the analysis processing for controlling this.

As described above, the medical image processing apparatus according to the present embodiment analyzes changes in the positional relationship of at least two sites that configure flexible sites such as joints, etc. by means of the bone objects corresponding to these sites. Moreover, in the same manner as Embodiment 2, in the medical image processing apparatus according to the present embodiment, the timing point specifying unit 512 is used as the external apparatus 51 to receive specifications at the desired timing point from among the series of timing points at which photographing by the X-ray photographing unit 500 was carried out, determining the positional relation of the bone corresponding to the timing point as the standard. On this basis, the medical image processing apparatus detects the timing point at which the amount of change of the positional relation of the bone in other timing points with respect to the standard became the standard value or more, and it controls the operation related to acquiring the projected data based on this timing point (that is, it changes the scanning conditions or stops scanning). Thereby, in the X-ray CT system according to the present embodiment, the X-ray CT system itself can automatically control the operation for acquiring projected data without the operator when the positional relationship of two or more sites satisfies specific conditions.

The image data according to the present embodiment is constructed so as to be capable of extracting bones. The flexible site is explained exemplifying a part configured by two bones as well as a joint connecting these bones. The joint is a joint connecting the bones and includes a joint fluid, a synovial, and a joint capsule; moreover, the side of the bone connected through the joint has cartilage and the flexible site can be smoothly moved by means of this cartilage. In other words, this bone also includes cartilage. In addition, this flexible site comprises a plurality of construction sites, and in the above case, these construction sites include two bones to be connected by the joint. Muscles are included as an example of flexible site in addition to bones.

Furthermore, the positional relation of components of the flexible site such as bones, etc. was described using the 2-dimensional positional relation between two bones as an example; however, the positional relation may be 3-dimensionally shaped in some cases. The example described a case when the first bone is pointing up and the second bone is pointing right, and when the second bone is pointing to the upper right with respect to this. However, a case may be considered in which the movement of the bone shifts in the rotational direction by adding a twist, etc., in addition to the movement in the 2-dimensional direction. A case may also be considered in which the position of the second bone does not move with respect to the first bone regardless of the rotation of the second bone. Accordingly, the positional relation of the components of the flexible site may be 3-dimensionally comprehended, the movement in the 3-dimensional rotational direction may be obtained from among the changes in the shape characteristics of three points and the shape feature of two points, thereby the amount of change in the positional relation is also obtained regarding the twisting, and the determination process with respect to the amount of change may be carried out. The determination process itself with respect to the amount of change is the same as in the case of the 2-dimensional positional relation.

In the above-described embodiments, as a flexible site, bones and joints are exemplified; however, as a flexible site, it is also possible to focus on cartilage. For example, the above-mentioned process may be carried out by identifying three points of shape features regarding cartilage and two shape features instead of identifying three points of shape features regarding the bones. As a merit of analyzing cartilage as a flexible site in place of a bone, improved diagnosis accuracy of disc hernias can be cited. Disc hernias occur due to the protrusion of cartilage in the joints.

Acquiring image data of cartilage by means of a medical imaging apparatus, the positional relationship of cartilage is analyzed in the same manner as the above-described positional relationship of the bones. Disc herniation is present if there is protrusion of cartilage in the joints; therefore, the diagnosis result may be obtained without having to wait for an analysis of the bone. This analysis processing can be carried out in place of analysis processing regarding the bones; however, the analysis processing can be carried out together with analysis processing regarding the bones. When acquisition and analysis of images are carried out in parallel with processing of the bones and it is found that a disk hernia has occurred from analysis results regarding images of the cartilage, by completing analysis without waiting for analysis of the bones, it is possible to acquire an accurate diagnosis at an earlier stage. Further, other than the case in which cartilage protrudes, the case in which cartilage is crushed by sites such as other bones is also considered; in this case also, when cartilage is crushed more than a certain extent, the crushing is defined as an analysis result, and based on this result, it is possible to change the frame rate, or the processing can shift to changing of the scanning conditions or stopping of the scan.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
a photographing unit configured to scan a flexible site of a living body having a plurality of components to obtain projected data,
a reconstruction processing unit configured to carry out reconstruction processing on the projected data to generate first image data regarding a plurality of timing points of the flexible site,
an extracting unit configured to extract a surface portion of the flexible site from the respective first image data regarding the plurality of timing points, and
an analyzing unit configured to compare the surface portion extracted from the first image data regarding the plurality of timing points with second image data showing the flexible site, to specify an image of the timing point shown in the second image data from among the first image data regarding the plurality of timing points.

2. The medical image processing apparatus according to claim 1, wherein
the analyzing unit is configured to specify a scan timing point of the first image data when a shape of the surface portion extracted from the first image data substantially coincides with a shape of the second image data, to be a timing point shown in the second image data.

3. The medical image processing apparatus according to claim 2, wherein
the analyzing unit is configured to specify a time width including the scan timing point as the timing point shown in the second image data, and
the reconstruction processing unit is configured to carry out reconstruction processing on the projected data at a first frame rate in order to generate the first image data of the flexible site, and after the time width is set by the analyzing unit, reconstruction processing is carried out at a second frame rate, which is different from the first frame rate, with respect to the projected data in a range corresponding to the time width from among the projected data, to generate the second image data.

4. The medical image processing apparatus according to claim 1, further comprising an extracting unit configured to extract the plurality of components configuring the flexible site from the respective first image data, wherein
the analyzing unit is configured to compare a positional relation of the components extracted from the respective first image data between a first timing point and another timing point other than the first timing point within a time in which the projected data was acquired, to determine a second timing point in which an amount of change of the positional relation is within a standard value, to be specified as the timing point shown in the second image data.

5. The medical image processing apparatus according to claim 4, wherein
the reconstruction processing unit is configured to carry out reconstruction processing on the projected data at a first frame rate to generate the first image data of the flexible site, and after the second timing point is determined, to carry out reconstruction processing on the projected data within the range corresponding to the second timing point from among the projected data at a second frame rate, which is different from the first frame rate, to generate the second image data.

6. The medical image processing apparatus according to claim 5, further comprising: a timing point specifying unit configured to specify the first timing point, in response to instructions from an apparatus connected outside.

7. The medical image processing apparatus according to claim 2, further comprising a controller configured to stop a generation of the projected data or a change of a projecting conditions using an X-ray photographing unit based on the scan timing point specified by the analyzing unit.

8. The medical image processing apparatus according to claim 4, further comprising a controller configured to stop a generation of the projected data or changes of projecting conditions using an X-ray photographing unit based on the second timing point obtained by the analyzing unit.

9. The medical image processing apparatus according to claim 4, wherein
the extracting unit is configured to respectively extract bones as the components, and
the analyzing unit is configured to obtain the positional relation of the components from the positional relation of the extracted bones.

10. The medical image processing apparatus according to claim 4, wherein
the analyzing unit is configured to shape two planes, each of which is shaped from three or more points of shape characteristics regarding each of the plurality of components, and obtain the positional relation of the plurality of components from the positional relation of the two shaped planes.

11. The medical image processing apparatus according to claim 10, wherein the analyzing unit is configured to calculate the amount of change from an angle configured from the two shaped planes.

12. The medical image processing apparatus according to claim 10, wherein the analyzing unit is configured to calculate the amount of change based on the distance between the two shaped planes.

13. The medical image processing apparatus according to claim 4, wherein the analyzing unit is configured to shape two lines by connecting two points of shape characteristics for each line regarding the respective components, and obtain the positional relation of the plurality of components from the positional relation of the two shaped lines.

14. The medical image processing apparatus according to claim 4, wherein the analyzing unit is configured to specify the positional relation of the plurality of components based on the outline of each of the plurality of components.

15. The medical image processing apparatus according to claim 4, wherein the analyzing unit is configured to specify the positional relation of the plurality of components based on information indicating a shade of each of the plurality of components.

16. The medical image processing apparatus according to claim 4, wherein the extracting unit is configured to extract the plurality of components based on the surface portion of the flexible site shown in the first image data.

17. The medical image processing apparatus according to claim 1, wherein
the extracting unit is configured to extract a region comprising the plurality of components configuring the flexible site based on the surface portion of the flexible site shown in the first image data, and
the analyzing unit is configured to compare the shape of the region extracted from the respective first image data between a first timing point and another timing point other than the first timing point within a time in which the projected data is acquired, to obtain a second timing point with an amount of change in shape of more than a standard value, to specify this as the timing point shown in the second image data.

18. The medical image processing apparatus according to claim 2, wherein the analyzing unit is configured to supplement information to the first image data corresponding to the scan timing points in order to differentiate from other timing points.

19. The medical image processing apparatus according to claim 4, wherein the analyzing unit is configured to supplement information to the image data corresponding to the second timing point in order to differentiate from other timing points.

20. The medical image processing apparatus according to claim 1, further comprising: an external photographing unit configured to photograph the flexible site and obtain the second image data showing the external image of the flexible site.

* * * * *